US012589147B2

(12) United States Patent
Langereis et al.

(10) Patent No.: US 12,589,147 B2
(45) Date of Patent: Mar. 31, 2026

(54) MULTIVALENT HVT VECTOR VACCINE

(71) Applicant: Intervet Inc., Madison, NJ (US)

(72) Inventors: Martijn Alexander Langereis, Gennep (NL); Iwan Verstegen, Boxmeer (NL)

(73) Assignee: Intervet Inc., Rahway, NJ (US)

( * ) Notice: Subject to any disclaimer, the term of this patent is extended or adjusted under 35 U.S.C. 154(b) by 876 days.

(21) Appl. No.: 17/784,838

(22) PCT Filed: Dec. 18, 2020

(86) PCT No.: PCT/EP2020/086940
§ 371 (c)(1),
(2) Date: Jun. 13, 2022

(87) PCT Pub. No.: WO2021/123104
PCT Pub. Date: Jun. 24, 2021

(65) Prior Publication Data
US 2023/0031097 A1 Feb. 2, 2023

(30) Foreign Application Priority Data

Dec. 20, 2019 (EP) .................................... 19218804

(51) Int. Cl.
| | |
|---|---|
| *A61K 39/295* | (2006.01) |
| *A61K 39/145* | (2006.01) |
| *A61K 39/17* | (2006.01) |
| *A61P 31/14* | (2006.01) |
| *A61P 31/16* | (2006.01) |
| *C12N 15/86* | (2006.01) |
| *A61K 39/00* | (2006.01) |

(52) U.S. Cl.
CPC .......... *A61K 39/295* (2013.01); *A61K 39/145* (2013.01); *A61K 39/17* (2013.01); *A61P 31/14* (2018.01); *A61P 31/16* (2018.01); *C12N 15/86* (2013.01); *A61K 2039/552* (2013.01); *A61K 2039/70* (2013.01); *C12N 2710/16034* (2013.01); *C12N 2710/16043* (2013.01); *C12N 2720/10034* (2013.01); *C12N 2760/16034* (2013.01); *C12N 2760/18134* (2013.01)

(58) Field of Classification Search
CPC .. C07K 14/195; C07K 2319/80; C12N 15/86; C12N 2740/16022; C12N 2740/16043; C12N 2710/16043; C12N 2710/16343; C12N 2720/10071; C12N 2710/16034; C12Q 1/18; G01N 2333/16; G01N 2333/165; G01N 2500/10; G01N 33/5091; A61K 2039/5256; A61K 2039/552; A61K 2039/70; A61K 39/12; A61K 39/145; A61K 39/17; A61K 39/245; A61K 39/295; A61P 31/12; A61P 31/16
See application file for complete search history.

(56) References Cited

U.S. PATENT DOCUMENTS

2008/0241188 A1 10/2008 Esaki et al.

FOREIGN PATENT DOCUMENTS

| | | | |
|---|---|---|---|
| CN | 106031793 A | 10/2016 | |
| CN | 107296956 A | 10/2017 | |
| EP | 0353809 A1 | 2/1990 | |
| EP | 0431668 B1 | 11/1990 | |
| EP | 1026246 A1 | 8/2000 | |
| JP | 2010532157 A | 10/2010 | |
| JP | 2015500806 A | 1/2015 | |
| RU | 2546247 C2 | 4/2015 | |
| RU | 2658439 C2 | 6/2018 | |
| RU | 2017126030 A | 1/2019 | |
| WO | 198704463 A1 | 7/1987 | |
| WO | 90/02803 A1 | 3/1990 | |
| WO | 1993025665 A1 | 12/1993 | |
| WO | 1996005291 A1 | 2/1996 | |
| WO | 1999018215 A1 | 4/1999 | |
| WO | WO-2008121329 A2 * | 10/2008 | .............. A61P 43/00 |
| WO | WO 2008121329 A3 | 10/2008 | |
| WO | WO 2010119112 A1 | 10/2010 | |
| WO | WO-2012052384 A1 * | 4/2012 | ........... A61K 39/145 |
| WO | 2013057236 A1 | 4/2013 | |
| WO | WO-2013082317 A2 * | 6/2013 | ............. C12N 15/86 |
| WO | WO 2013082317 A3 | 6/2013 | |
| WO | WO 2013082327 A1 | 6/2013 | |
| WO | 2013144355 A1 | 10/2013 | |
| WO | 2016087560 A1 | 6/2016 | |

(Continued)

OTHER PUBLICATIONS

Afonso et al., 2001, "The genome of turkey herpesvirus," J. Virol., 75(2):971-978.
Capua, Ilaria, Three open issues on Avian Influenza—H5, H7, H9 against all odds, British Poultry Science, 2013, 1-4, 54(1).
Cronenberg, A.M. et al., Vaccination of Broilers With HVT. Expressing An. Eimer/A Acervulina Antigen Improves Performance After Challenge With Eimer/A, Acta virologica, 1999, 192-197, 43.
Hall, R.N., et al., Identification of non-essential loci within the Meleagrid herpesvirus 1 genome, Virology Journal, 2015, pp. 1-12, DOI 10.1186/s12985-015-0362-9.

(Continued)

*Primary Examiner* — Bao Q Li
(74) *Attorney, Agent, or Firm* — Susanna C. Benn

(57) ABSTRACT

The present invention describes a recombinant herpesvirus of turkeys (rHVT) that can be used as a vector vaccine for poultry against infection and disease from multiple poultry pathogens. Specifically the rHVT expresses an infectious bursal disease virus (IBDV) viral protein 2 (VP2) gene and a Newcastle disease virus (NDV) fusion (F) protein gene from a first and a second expression cassette inserted in the unique small (Us) region, and expresses an avian influenza vims (AIV) haemagglutinin (HA) gene from a third expression cassette inserted in the unique long (UL) region of the genome of said rHVT either between the UL40 and UL41 genes, or between the UL44 and UL45 genes. This rHVT can be used to vaccinate poultry against MDV, IBDV, NDV and AIV.

20 Claims, No Drawings
Specification includes a Sequence Listing.

(56) References Cited

FOREIGN PATENT DOCUMENTS

| WO | 2016102647 | A1 | 6/2016 |
| WO | 2018112051 | A1 | 6/2018 |
| WO | 2019072964 | A1 | 4/2019 |

OTHER PUBLICATIONS

Kingham, et al., The Genome of Herpesvirus of Turkeys: Comparative Analysis with Marek's Disease Viruses, Journal of General Virology, 2001, 1123-1135, 82.

Koedood, M. et al., Human Cytomegalovirus (HCMV) Immediate-Early Enhancer/Promoter Specificity during. Embryogenesis Defines Target Tissues of Congenital HCMV Infection, Journal of Virology, 1995, pp. 2194-2207, Vo. 69, No. 4.

Pederson, et al., Analysis of the GB promoter of herpes simplex virus type 1: high-level expression requires both an 89-base-pair promoter fragment and a nontranslated leader sequence., Journal of Virology, 1992, pp. 6226-6232, vol. 66, No. 10.

Pereira, Lenore, Function of Glycoprotein B Homologues of the Family Herpesviridae, Infectious Agents and Disease, 1994, 9-28, 3.

Tang, N., et al., A simple and rapid approach to develop recombinant avian herpesvirus vectored vaccines using CRISPR/Cas9 system, Vaccine, 2018, pp. 716-722, 36.

* cited by examiner

MULTIVALENT HVT VECTOR VACCINE

CROSS-REFERENCE TO RELATED APPLICATIONS

This application is a National Stage application of International Patent Application No. PCT/EP2020/086940 filed Dec. 18, 2020, which claims priority to European Provisional Patent Application No. 19218804.3, filed Dec. 20, 2019.

The present invention relates to the field of veterinary vaccines, namely to vaccines for poultry based on a recombinant herpesvirus of turkeys as viral vector vaccine. In particular the invention relates to a recombinant herpesvirus of turkeys (rHVT), to a host cell comprising said rHVT, to medical uses of said rHVT and said host cell, to vaccines comprising the rHVT and/or the host cell, and to methods for the production of said vaccines.

Recombinant vector viruses are a well-known way to express a heterologous gene and deliver its protein product to a human- or non-human animal target. Examples are Vacciniavirus- or Adenovirus vectors. When the heterologous gene encodes an immunogenic protein from a pathogen, this can be a way of effective vaccination of the target against disease caused by that pathogen. As a replicative micro-organism the vector virus can establish a productive infection in a vaccinated target, expressing the heterologous gene along with its own genes, and in this way stimulate the target's immune system.

In veterinary vaccination, and especially for the vaccination of poultry, vector vaccines have gained interest for their relative ease of use and low costs. Several avian vector vaccines have been considered over time, for example based on fowl adenovirus, fowlpox virus, and in particular on Herpesvirus of turkeys (HVT), see WO 87/04463 and WO 90/002803. An advantage of using HVT as a vector, is that it is non-pathogenic to avians, while it does induce an immunity against pathogenic members of its viral family: Marek's disease virus 1 or 2 (MDV1 or MDV2).

Over the years genes from different avian pathogens have been expressed in HVT vectors, such as from: Newcastle disease virus (NDV), infectious bursal disease virus (IBDV), infectious laryngotracheitis virus (ILTV), and infectious bronchitis virus, see: WO 93/025665; avian influenza virus (AIV) see WO 2012/052384; or from the parasite *Eimeria* (Cronenberg et al., 1999, Acta Virol., vol. 43, p. 192-197). This has led to the development of a variety of commercial HVT vector vaccines for poultry, for instance: against ND: Innovax®-ND (MSD Animal Health), and Vectormune™ HVT-NDV (Ceva Santé Animale); against ILT: Innovax®-ILT (MSD Animal Health); against IBD: Vaxxitek™ HVT+IBD (Boehringer-Ingelheim; previously named: Gallivac™ HVT-IBD), and Vectormune® ND (Ceva Santé Animale); and against AI: Vectormune® AI (Ceva Santé Animale).

The insertion of a heterologous gene into its viral genome is a burden on the vector virus. This may affect its replication, expression, and/or its genetic stability, in vitro and/or in vivo. These issues are particularly prominent when more than one heterologous gene is inserted. Such a multivalent recombinant vector vaccine can potentially protect against multiple diseases after a single inoculation. However such a vector construct must still provide a good replication of the vector and of its inserts, both in vitro and in vivo, and an effective expression of all the heterologous genes, at sufficiently high level, and over a significant period of time, to induce and maintain a protective immune-response in a vaccinated target against all intended pathogens.

This stability of replication and of expression will also allow for the extensive rounds of replication in vitro that are necessary for large scale production. In addition, such stability is a requirement to provide compliance with the very high standards of safety and biological stability that must be met by a recombinant virus (being a genetically modified organism) in vivo, to be awarded a marketing authorisation from governmental- or regulatory authorities, before it can be introduced into the field as a commercial product.

Many multivalent HVT vector vaccines have been described over time, e.g. as in: WO 93/025665 and WO 96/005291. However most of the multi-gene constructs described in such publications are only suggested, and only some of the recombinant vectors with multiple inserts were actually constructed and isolated. Very few were ever tested in birds. Overall no results are given on their stability upon replication, or the expression levels of the foreign genes, let alone any data on the induction of an effective immune protection in target animals. It is because of such challenges with the genetic stability and continued expression of the inserts that only very few multivalent HVT vector constructs have actually made it to become licensed and commercially available vaccine products. Currently these are: Innovax® ND-IBD (MSD Animal Health; WO 2016/102647), Innovax® ND-ILT ((MSD Animal Health; WO 2013/057236), ULTIFEND™ IBD ND (Ceva Santé Animale; WO 2013/144355), and Vaxxitek® HVT+IBD+ND (Boehringer-Ingelheim; WO 2018/112.051). Also, WO 2019/072964 describes a vaccine of a multivalent rHVT vector that is able to protect against MDV, NDV, IBDV and ILTV.

However as there are many more prominent poultry diseases in need of effective vaccination, there is an ongoing need for further multivalent vector vaccines.

WO 1999/018215 describes multivalent HVT vector constructs with inserts of NDV-F or HN genes and of IBDV-VP2 genes. Several possible insertion sites are described, among which between the UL40 and UL41 genes of HVT. However the only recombinant HVT (rHVT) constructs actually made, have an insert between the HVT genes UL44 and UL45 or between UL45 and UL46. No data is provided on the genetic stability of any of the vector's described.

WO 2012/052384 describes an rHVT expressing an AIV HA gene driven by a glycoprotein B (gB) gene promoter from a mammalian herpesvirus, from a locus in the unique small (Us) genome region.

WO 2016/102647 describes a multivalent rHVT expressing an NDV F gene and an IBDV VP2 gene from a single expression cassette which is inserted in the Us genome region.

It is an object of the present invention to accommodate to this need in the field, and to provide, for the first time, an rHVT vector vaccine that enables the immunisation of poultry against the 4 avian pathogens: MDV, NDV, IBDV and AIV, from a single vaccination.

Surprisingly it was found that this object can be met, and consequently one or more disadvantages of the prior art can be overcome, by providing an rHVT that expresses the NDV F and the IBDV VP2 genes from its Us genome region, and the AIV HA gene from its UL genome region.

The inventors attempted to extend the number of heterologous gene inserts in an existing rHVT that already contained two heterologous genes: NDV F and IBDV VP2, both expressed from the virus' Us region ("rHVT-VP2-F"). The additional heterologous gene selected was the AIV HA gene. The inventors tested a series of constructs where the HA gene was inserted in different insertion sites in the HVT genome. Unfortunately they found that several of the insertion sites tested did not allow the generation of a stable multivalent recombinant virus, as they did not generate an HVT stably replicating and expressing the three inserted heterologous genes. For example, not successful was the insertion of an HA gene into the UL genome region of the rHVT-VP2-F in between the UL47 and UL48 genes, or between the UL54 and LORF4 genes. When tested after 16 passages in cell culture, both these constructs showed several plaques that had lost the expression for one or two of the heterologous genes. This was remarkable, because these genes were not known to be essential for HVT. In fact UL47 and UL48 were reported to be non-essential in a transposon gene knock-out study of the HVT genome (Hall et al., 2015, Virology Journal, vol. 12, p. 130).

Clearly, the fact that the parental vector already expressed two other heterologous genes complicated things to such an extent that no predictions could be based on observations in the prior art on what was an allowable insertion site for an additional heterologous gene in the HVT genome.

It was therefore unexpected that two other insertion sites in the HVT UL genome region could be used for the insertion of the additional heterologous gene, namely: between the UL40 and UL41 genes of HVT or between the UL44 and UL45 genes of HVT; referred to herein as the "UL40-41" and the "UL44-45" loci, respectively.

The resulting multivalent rHVT vectors having the HA gene in the UL40-41 or in the UL44-45 locus, were found to be genetically stable, even after 16 consecutive passages in an in vitro cell culture. The 16th passage viruses were subsequently used for the vaccination of chickens, which accounts for several further replication cycles in vivo. Virus was then re-isolated from vaccinated chickens at 11 and at 32 days post vaccination, and analysed for maintaining the expression of the inserted genes. From both time points, the re-isolated viruses were found to be fully genetically stable: in immuno-fluorescence plaque assay all re-isolated viruses studied demonstrated expression of all three heterologous genes: F, VP2 and HA. No plaques were observed that were non-fluorescing for any one of the heterologous inserts.

The vaccinated chickens showed excellent seroconversion against each of the expressed antigens: F, VP2 and HA. Antibody levels reached against each of the three antigens were well above those that are known to be required for in vivo protection against challenge. Details are provided in the Examples.

Therefore these new multivalent rHVT vector viruses are stable, and are useful as vaccines against one, or more, or all of MDV, NDV, IBDV, and AIV.

The possibility to obtain a vaccination against 4 major poultry diseases from a single inoculation, is hugely beneficial, as it represents an important reduction of stress for the target animals, as well as a reduction of efforts and costs for the poultry farmer.

It is not known exactly how or why an rHVT expressing a VP2 and an F gene can tolerate the additional AIV HA gene in the UL40-41 or in the UL44-45 insertion site, whereas insertion in other sites, that would at first instance appear to be suitable, did not result in stable and effective vector constructs.

Although the inventors do not want to be bound by any theory or model that might explain these findings, they assume that this effect results from the complex interaction of the various expression patterns in the multivalent rHVT, when this is required to replicate and express in vitro and in vivo. For unknown reasons the insertion of the additional gene at specific sites results in a multivalent rHVT that has just the right balance between the strength of expression of the heterologous genes, and the strain this puts on the replicative capacity of the HVT itself, whereas other constructs (unpredictably) do not.

Therefore in one aspect the invention relates to a recombinant herpesvirus of turkeys (rHVT) expressing an infectious bursal disease virus (IBDV) viral protein 2 (VP2) gene and a Newcastle disease virus (NDV) fusion (F) protein gene from a first and a second expression cassette which are inserted in the unique small (Us) region of the genome of said rHVT, characterised in that said rHVT also expresses an avian influenza virus (AIV) haemagglutinin (HA) gene from a third expression cassette which is inserted in the unique long (UL) region of the genome of said rHVT either between the UL40 and UL41 genes, or between the UL44 and UL45 genes.

A "recombinant" is a nucleic acid molecule or a microorganism of which the genetic material has been modified relative to its starting- or native condition, to result in a genetic make-up that it did not originally possess.

"Herpesvirus of turkeys (HVT)" is also called MDV3, Meleagrid herpesvirus 1, or turkey herpesvirus. HVT was first described in 1970 (Witter et al., 1970, Am. J. Vet. Res., vol. 31, p. 525). Well-known strains of HVT such as PB1 or FC-126 have for a long time been used as live vaccines for poultry against Marek's disease caused by MDV1 or MDV2.

Herpesvirus of turkeys, Newcastle disease virus, infectious bursal disease virus, and avian influenza virus, are all well-known viruses of veterinary relevance. The same applies to cytomegalovirus (CMV), simian virus 40 (SV40), feline herpesvirus (FHV) and pseudorabies virus (PRV). Such a virus has the characterising features of its taxonomic group, such as the morphologic, genomic, and biochemical characteristics, as well as the biological characteristics such as physiologic, immunologic, or pathologic behaviour.

General information on these viruses is available e.g. from reference handbooks such as Fields Virology (LWW publ., ISBN: 9781451105636). Information on diseases caused by these viruses is available e.g. from handbooks like: The Merck veterinary manual (2010, 10th ed., 2010, C. M. Kahn edt., ISBN: 091191093X), and: 'Diseases of poultry' (2008, 12th ed., Y. Saif ed., Iowa State Univ. press, ISBN-10: 0813807182). Samples of these viruses for use in the invention can be obtained from a variety of sources, e.g. as a field isolate from a human, or from a non-human animal in the wild or on a farm, or from various laboratories, (depository) institutions, or (veterinary) universities. The viruses can be readily identified using routine serological- or molecular biological tools. From all these viruses much genetic information is available digitally in public sequence databases such as NCBL's GenBank and EMBL's EBI.

As is known in the field, the classification of a microorganism in a particular taxonomic group is based on a combination of its features. The invention therefore also includes variants in the virus' species that are sub-classified therefrom in any way, for instance as a subspecies, strain, isolate, genotype, variant, subtype or subgroup, and the like.

Further, it will be apparent to a person skilled in the field of the invention that while a particular virus for the invention may currently be assigned to this species, that is a taxonomic classification that could change in time as new insights can lead to reclassification into a new or different taxonomic group.

However, as this does not change the virus itself, or its antigenic repertoire, but only it's scientific name or classification, such re-classified viruses remain within the scope of the invention.

A "VP2 protein gene" is well-known, encoding the IBDV's capsid protein. A VP2 protein gene may be derived from a classic-, or from a variant type IBDV, or may be chimeric.

Similarly an "F protein gene" is well-known in the art, encoding the NDV's immunodominant fusion-glycoprotein. For the invention, the F protein gene can be obtained from a lentogenic, mesogenic, or velogenic type of NDV, or may be chimeric.

The term "expressing" refers to the well-known principle of gene expression wherein genetic information provides the code for the production of a protein, via transcription and translation.

The term "gene" is used to indicate a section of nucleic acid that is capable of encoding a protein. For the invention this corresponds to an 'open reading frame' (ORF), i.e. a section of DNA between a start- and a stop-codon, not including the gene's promoter. A gene for the invention may encode a complete protein, or may encode a section of a protein, for example encoding only the mature form of a protein, i.e. without a 'leader', 'anchor', or 'signal sequence'. A gene may even encode a specific section of a protein, e.g. a section comprising an immunoprotective epitope.

In this regard a "protein" for the invention is a molecular chain of amino acids. The protein can be a native or a mature protein, a pre- or pro-protein, or a functional fragment of a protein. Therefore peptides, oligopeptides and polypeptides are included within the definition of protein, as long as these still contain a relevant immunological epitope and/or a functional region.

For the invention, a gene is "heterologous" to the rHVT vector that carries it, if that gene was not present in the parental HVT that was used to generate the rHVT vector.

An "expression cassette" is a nucleic acid fragment comprising at least one heterologous gene and a promoter to drive the transcription of that gene. The termination of the transcription may be provided by sequences provided by the genomic insertion site of the cassette, or the expression cassette can itself comprise a termination signal, such as a transcription terminator.

In such a cassette, both the promoter and the terminator need to be in close proximity to the gene of which they regulate the expression; this is termed being 'operatively linked', whereby no significant other sequences are present between them that would intervene with an effective start respectively termination of the transcription.

While the expression cassette can exist in DNA or in RNA form, because of its intended use in an HVT vector, therefore the expression cassette for the invention is employed as DNA. As will be apparent to a skilled person, an expression cassette is a self-contained expression module, therefore its orientation in a vector virus genome is generally not critical.

Optionally the expression cassette may contain further DNA elements, for example to assist with the construction and cloning, such as sites for restriction enzyme recognition or PCR primers.

An expression cassette as a whole is inserted into a single locus in the vector's genome. Different techniques are available to control the locus and the orientation of that insertion. For example by using the appropriate flanking sections from the genome of the vector to integrate the cassette by a homologous recombination process, e.g. by using overlapping cosmids as described in U.S. Pat. No. 5,961,982. Alternatively the integration may be done by using the CRISPR/Cas9 technology as described below.

For the invention, an "insert", or an "inserted" expression cassette in a vector's genome, refers to the integration into the vector's genomic nucleic acid so that the inserted element gets transcribed and translated along with the vector's native genes. The effect on the vector's genome differs depending on the way the insertion is made: the vector genome may become larger, the same, or smaller in size, depending from whether the net result on the genome is an addition, replacement or deletion of genetic material, respectively. The skilled person is perfectly able to select and implement a certain type of insertion, and make adaptations when needed.

The construction of an expression cassette and its insertion into an HVT vector can be done by well-known molecular biological techniques, involving cloning, transfection, recombination, selection, and amplification. These, and other techniques are explained in great detail in standard text-books like Sambrook & Russell: "Molecular cloning: a laboratory manual" (2001, Cold Spring Harbour Laboratory Press; ISBN: 0879695773); Ausubel et al., in: Current Protocols in Molecular Biology (J. Wiley and Sons Inc, N Y, 2003, ISBN: 047150338X); and C. Dieffenbach & G. Dveksler: "PCR primers: a laboratory manual" (CSHL Press, ISBN 0879696540); and "PCR protocols", by: J. Bartlett and D. Stirling (Humana press, ISBN: 0896036421).

For the invention, the terms 'first', 'second', and 'third' in regard to the expression cassettes are only used for ease of reference, and not to indicate any order or preference.

The "unique small (Us) region" of the HVT genome is well-known to be the downstream section of the genome between the 'internal repeat short', and the 'terminal repeat short'. The HVT Us is about 8.6 kb in size (see: Kingham et al., 2001, J. of Gen. Virol., vol. 82, p. 1123-1135).

The fully annotated genome sequence of well-known HVT strain FC-126 is for example available as GenBank accession number: AF291866, wherein nucleotides 5910-117777 are the UL region, and nucleotides 136990-145606 are the Us region.

A "haemagglutinin (HA) protein gene" encodes the AIV main antigen. The HA protein can be any one of the known serotype variants, currently: H1-H18, or can be a chimera. Highly pathogenic AIV have an HA that is of the H5 or H7 serotype.

The "unique long (UL)" region of the HVT genome is the upstream part of the genome, and in HVT is about 110 kb in size.

The indication "UL40" is well-known in the field of the invention to refer to a specific gene located in the UL genome region, see e.g. GenBank accession number: AF291866. The same (mutatis mutandis) applies for the indications "UL41", "UL44", and "UL45".

The term "between" serves to indicate that the inserted expression cassette is placed in an insertion site (i.e. a locus) on the HVT genome that is outside of the coding sequence for the indicated genes, thus not in the open reading frames for UL40, 41, 44 or 45. Such a region is also called an inter-genic region.

Details of embodiments and of further aspects of the invention will be described below.

Preferably the cassette expressing the IBDV VP2 gene has specific elements.

In an embodiment the rHVT according to the invention is characterised in that the IBDV VP2 is expressed from a first expression cassette comprising in 5' to 3' direction and in this order:

a. a murine cytomegalovirus immediate early 1 gene (mCMV-IE1) promoter, b. an IBDV VP2 gene, and c. a transcription terminator, and whereby the promoter and the terminator of said expression cassette are operatively linked to the VP2 gene.

The term "comprising" (as well as variations such as "comprises", "comprise", and "comprised") as used herein, intends to refer to all elements, and in any possible combination conceivable for the invention, that are covered by or included in the text section, paragraph, claim, etc., in which this term is used, even if such elements or combinations are not explicitly recited; and not to the exclusion of any of such element(s) or combinations.

Therefore any such text section, paragraph, claim, etc., can therefore also relate to one or more embodiment(s) wherein the term "comprising" (or its variants) is replaced by terms such as "consist of", "consisting of", or "consist essentially of".

The term "in 5' to 3' direction", also known as: 'in downstream direction', is well-known in the field. Together with the terms "in this order" it serves to indicate the relative orientation which the elements that are summed up thereafter need to have in respect of each other, in order to be functional with the gene-expression machinery of a host cell in which a rHVT according to the invention comprising the expression cassette can be replicated and expressed. As the skilled person will realise, this direction relates to the DNA strand from the double stranded DNA genome of HVT that is the 'coding strand', and it relates to the encoded mRNA molecule that is in the '+' or 'sense' orientation.

Nevertheless, and without prejudice to the section above: on the complementary strand of the HVT ds DNA genome, the 'template' strand, the relative order of the listed elements is the same, but on that DNA strand the direction of these elements is 3' to 5'.

A "promoter" for the invention is well-known to be a functional region of genetic information that directs the transcription of a downstream coding region. A promoter is thus situated upstream of a gene.

The nomenclature for a promoter is commonly based on the gene of which it controls the expression. For example, the term "mCMV-IE1 gene promoter" as used herein, refers to the promoter that in nature drives the expression of the IE1 gene from mCMV, and is thus situated immediately upstream of that gene in the mCMV genome. Because the IE1 gene is such a well-documented and clearly recognisable gene, and because the genomes of several mCMV have been sequenced, such a promoter can readily be identified by routine techniques. For example, in a basic protocol a promoter can simply be obtained by roughly subcloning the region in between two consecutive genes, e.g. from the poly A signal of an upstream gene to the transcription start-signal of a downstream gene. The promoter can then be identified by standard tests, e.g. by the expression of a marker gene using progressively smaller sections of a nucleic acid region containing a suspected promoter.

Commonly promoters contain a number of recognisable, regulatory regions, such as the enhancer region, which is involved in binding regulatory factors that influence the time, the duration, the conditions, and the level of transcription. While the enhancer region is commonly situated upstream of a promoter, a promoter can also be influenced by regions more downstream towards the start codon that are involved in the binding of transcription factors and directing the RNA polymerase itself. Such a region generally contains a number of conserved promoter sequence elements such as the TATA box, the CAAT box, and the GC box.

A promoter comprising both the enhancer- and the downstream region is termed a "complete" promoter; a promoter comprising only the downstream region, is termed a "core" promoter.

A "transcription terminator" is a regulatory DNA element involved in the termination of the transcription of a coding region into RNA. Commonly such an element encodes a section with a secondary structure, e.g. a hairpin, that can cause the RNA polymerase complex to strop transcription. A transcription terminator is therefore always situated downstream from the stop codon of the region to be translated, the '3' untranslated region'. A terminator can also comprise a poly-adenylation (polyA) signal. This induces the polyadenylation that occurs to most eukaryotic mRNA's, and which is relevant for the transportation and stability of mRNA molecules.

The mCMV-IE1-gene is well-known in the art, and can be readily obtained from a variety of commercial sources, such as from suppliers of commercial plasmids for cloning and expression. The IE1 gene is also called the 'major IE gene' of CMV.

The mCMV-IE1 protein is also called pp89. The mCMV IE1 gene promoter was described in 1985 (K. Dörsch-Häsler, et al., 1985, PNAS, vol. 82, p. 8325). Use of this promoter in heterologous expression is described in WO 87/03.905 and EP 728.842. The nucleotide sequence of the complete mCMV IE gene locus is available from GenBank under acc. nr. L06816.1 (from March 2004). The mCMV itself is available from the ATCC under acc. nr. VR-1399.

In an embodiment of the rHVT according to the invention, in the first expression cassette the mCMV-IE1 gene promoter is a complete promoter, comprising both the core promoter region, as well as the enhancer region for the mCMV-IE1 gene. The complete mCMV-IE1 gene promoter is about 1.4 kb in size.

The term "about" for the invention means±25% around an indicated value, preferably "about" means±20, 15, 12, 10, 8, 6, 5, 4, 3, 2% around an indicated value, or even "about" means±1% around an indicated value, in that order of preference.

In an embodiment the mCMV-IE1 gene promoter for the invention is a DNA molecule of about 1.4 kb, comprising a nucleotide sequence that has at least 95% nucleotide sequence identity to the full length of the region of nucleotides 1-1391 of SEQ ID NO: 1. More preferred is a nucleotide sequence identity of at least 96, 97, 98, or even 99%, in that order of preference.

In an embodiment, the mCMV-IE1 gene promoter is the region of nucleotides 1-1391 of SEQ ID NO: 1.

In an embodiment of the rHVT according to the invention, in the first expression cassette the IBDV VP2 gene for the invention encodes a VP2 protein from an IBDV that is of the classic type. Such genes are well-known and their sequence information is readily available in the prior art, see e.g. GenBank acc.nr: D00869 (strain F52/70), D00499 (STC), or AF499929 (D78). Alternatively, this gene can be obtained from the genome of a classic IBDV isolated from nature, using routine techniques for manipulating a Birnavirus. Classic type IBDV's can be readily identified using serology, or molecular biology.

As homologs or variants of the IBDV VP2 gene may have equal efficacy and stability, therefore in an embodiment, the IBDV VP2 protein gene for the invention has at least 90% nucleotide sequence identity to the full length of the region of nucleotides 1423-2781 of SEQ ID NO: 1. Preferred is a nucleotide sequence identity of at least 92, 94, 95, 96, 97, 98, or even 99%, in that order of preference.

In an embodiment the IBDV VP2 protein gene for the invention is derived from the classic IBDV strain Faragher 52/70.

In an embodiment the IBDV VP2 protein gene for the invention is the region of nucleotides 1423-2781 of SEQ ID NO: 1.

For the expression cassettes for the invention, the selection of a specific type of transcription terminator is not critical, as long as effective termination of RNA transcription is provided.

In an embodiment of the rHVT according to the invention, the first, second, and/or the third expression cassette for the invention comprise a transcription terminator which comprises both a terminator region and a polyA region.

In an embodiment of the rHVT according to the invention, in the first expression cassette the transcription terminator is derived from simian virus 40 (SV40), preferably from the SV40 late gene.

This terminator and its use in heterologous expression, is available via the commercial 'pCMVß' cloning plasmids (Clontech), since the late 1980's.

In an embodiment of the rHVT according to the invention, in the first expression cassette the transcription terminator is derived from the SV40 late gene and is about 0.2 kb in size, and comprises a nucleotide sequence that has at least 95% nucleotide sequence identity to the full length of the region of nucleotides 2812-3021 of SEQ ID NO: 1. More preferred is a nucleotide sequence identity of at least 96, 97, 98, or even 99%, in that order of preference.

In an embodiment, the transcription terminator from the SV40 late gene is the region of nucleotides 2812-3021 of SEQ ID NO: 1.

In an embodiment of the rHVT according to the invention, for the first expression cassette one or more or all of the conditions apply selected from the group consisting of:

the mCMV-IE1 gene promoter is a complete promoter;

the IBDV VP2 gene encodes a VP2 protein from a classic type IBDV; and the first transcription terminator comprises both a terminator region and a polyA region; preferably the transcription terminator is derived from SV40.

In an embodiment of the rHVT according to the invention, the first expression cassette is the region of nucleotides 1-3021 of SEQ ID NO: 1.

Preferably the cassette expressing the NDV F gene has specific elements.

In an embodiment the rHVT according to the invention is characterised in that the NDV F gene is expressed from a second expression cassette comprising in 5' to 3' direction and in this order:

a. a human cytomegalovirus immediate early 1 gene (hCMV-IE1) promoter, b. an NDV F protein gene, and c. a transcription terminator, and whereby the promoter and the terminator of said expression cassette are operatively linked to the F gene.

The hCMV-IE1 gene promoter in its complete version is about 1.5 kb in size and consists of an enhancer, a core promoter, and an intron, whereby the promoter activity proceeds into the intron region, see Koedood et al. (1995, J. of Virol., vol. 69, p. 2194-2207).

An hCMV-IE1 gene promoter can be obtained from the genome of an hCMV virus (which are widely available), by subcloning the genomic area preceding the IE1 gene, using routine molecular biological tools and methods. Alternatively the promoter can be derived for example from commercial expression plasmids, such as p117, described by Cox et al. (2002, Scand. J. Immunol., vol. 55, p. 14-23), or from commercially available mammalian expression vectors such as the pCMV (Clontech), or the pCMV-MCS series (Stratagene; GenBank™ acc. nr. AF369966). The genome sequence of hCMV is for example available from GenBank accession number X17403.

From the hCMV-IE1 gene promoter, many highly similar versions are known, e.g. from GenBank. Such homologs and variants are within the scope of the invention.

In an embodiment of the rHVT according to the invention, in the second expression cassette for the invention, the hCMV-IE1 gene promoter is a core promoter. Such a core promoter will typically be smaller than 1 kb in size; preferably about 0.4 kb in size.

In an embodiment the hCMV-IE1 gene core promoter for the invention is a DNA molecule of about 0.4 kb, comprising a nucleotide sequence that has at least 95% nucleotide sequence identity to the full length of the region of nucleotides 3160-3520 of SEQ ID NO: 1. More preferred is a nucleotide sequence identity of at least 96, 97, 98, or even 99%, in that order of preference.

In an embodiment, the hCMV-IE1 gene core promoter is the region of nucleotides 3160-3520 of SEQ ID NO: 1.

In an embodiment of the rHVT according to the invention, in the second expression cassette for the invention, the NDV F protein gene is from an NDV that is of the lentogenic type.

Preferably the NDV F protein gene from a lentogenic NDV strain, is from NDV strain Clone 30. NDV Clone 30 is a well-known lentogenic type NDV that has been used for many years as a live vaccine, e.g. as Nobilis® ND Clone 30 (MSD Animal Health).

In an embodiment, the NDV F protein gene for the invention has at least 90% nucleotide sequence identity to the full length of the region of nucleotides 3545-5206 of SEQ ID NO: 1. Preferably a nucleotide sequence identity of at least 92, 94, 95, 96, 97, 98, or even 99%, in that order of preference.

In an embodiment the NDV F protein gene for the invention is the region of nucleotides 3545-5206 of SEQ ID NO: 1.

In an embodiment of the rHVT according to the invention, in the second expression cassette for the invention, the transcription terminator is derived from the hCMV-IE1 gene. Preferably this transcription terminator is about 0.3 kb in size.

In an embodiment the transcription terminator is derived from the hCMV-IE1 gene, is about 0.3 kb in size, and comprises a nucleotide sequence that has at least 95% nucleotide sequence identity to the full length of the region of nucleotides 5218-5498 of SEQ ID NO: 1. More preferred is a nucleotide sequence identity of at least 96, 97, 98, or even 99%, in that order of preference.

In an embodiment of the rHVT according to the invention, the transcription terminator derived from the hCMV-IE1 gene is the region of nucleotides 5218-5498 of SEQ ID NO: 1.

In an embodiment of the rHVT according to the invention, for the second expression cassette one or more or all of the conditions apply selected from the group consisting of:

the hCMV-IE1 gene promoter is a core promoter;

the NDV F gene is from a lentogenic NDV strain, preferably from NDV strain Clone 30; and the transcription terminator is derived from the hCMV-IE1 gene.

In an embodiment of the rHVT according to the invention, the second expression cassette is the region of nucleotides 3160-5498 of SEQ ID NO: 1.

Because an expression cassette is a self-contained expression module, as described, therefore the first and the second expression cassettes for the invention can be inserted in the Us genome region of the rHVT according to the invention in different loci and in different orientations. These loci can be the same or different from each other.

In an embodiment the rHVT according to the invention is characterised in that the first and the second expression cassette are inserted in the same locus or in different loci of the Us region of the genome of said rHVT.

Several genetic loci of the HVT Us genome region have been demonstrated to allow the insertion of one or more heterologous genes, see e.g. EP 431.668 and WO 2016/102647. For example: Us2, Us10, the region between Us10 and SORF3, and the region between Us2 and SORF3.

Therefore in an embodiment the rHVT according to the invention is characterised in that the first and the second expression cassette are both inserted in the Us2 gene, or are both inserted in the Us10 gene, or one is inserted in the Us2 gene and the other is inserted in the Us10 gene.

The consequence of such insertion is that the normal coding function of the Us2 respectively the Us10 gene is disturbed, or even completely abolished in the resulting rHVT.

For ease of assembly of an rHVT according to the invention, the first and the second expression cassettes for the invention, can be combined into one single expression cassette. This can conveniently be inserted in a locus of the HVT Us genome region.

Therefore in an embodiment the rHVT according to the invention is characterised in that the first and the second expression cassette are combined into a single expression cassette.

Because the first and the second cassettes for the invention comprise their own promoter and terminator elements, therefore they can be oriented relative to each other in different ways, when in the combined single expression cassette for the invention. Specifically these orientations can be: 'head to head', 'tail to tail', and in 2 orientations of 'tail to head'; all well-known in the field of the invention.

In a preferred embodiment of the rHVT according to the invention, having the first and the second expression cassette combined into a single expression cassette, the first and the second expression cassette are oriented tail to head, whereby the VP2 gene is located upstream of the F gene.

In a more preferred embodiment the combined single expression cassette is an expression cassette as disclosed in WO 2016/102647.

Even more preferably the combined single expression cassette is the cassette as employed in the rHVT construct described in WO 2016/102647 as HVP360, which is available commercially as Innovax® ND-IBD (MSD Animal Health).

Therefore, in an embodiment of the rHVT according to the invention, the combined single expression cassette comprises in 5' to 3' direction and in this order:

a. an mCMV-IE1 promoter,
b. an IBDV VP2 gene,
c. a transcription terminator,
d. an hCMV-IE1 promoter,
e. an NDV F protein gene, and
f. a transcription terminator, and whereby the promoters and terminators are operatively linked to their corresponding genes.

In the combined single expression cassette for the invention, the transcription terminator element c. between the VP2 and the F genes, provides for an effective separation of their expression, by preventing possible read-through of RNA transcription.

Both terminators indicated for the combined single expression cassette may be the same, or may be different.

With "the promoters and terminators are operatively linked to their corresponding genes", is indicated that promoter a. and terminator c. are operatively linked to gene b.; and similarly: promoter d. and terminator f. are operatively linked to gene e.

An example of a combined single expression cassette for the invention is presented in SEQ ID NO: 1, the elements of which are described in Table 1.

TABLE 1

| Elements of SEQ ID NO: 1 | | |
|---|---|---|
| Nucleotide region | | Elements of SEQ ID NO: 1 |
| 1 | 1391 | mCMV-IE1 gene promoter + enhancer |
| 1423 | 2781 | IBDV strain F 52/70, VP2 gene |
| 2812 | 3021 | SV40 late gene terminator + polyA signal |
| 3160 | 3520 | hCMV-IE1 gene core promoter |
| 3545 | 5206 | NDV Clone 30 F-gene |
| 5218 | 5498 | hCMV IE1 gene terminator |

In an embodiment, the single combined expression cassette for the invention is about 5.5 kb in size.

In an embodiment of the rHVT according to the invention, the combined single expression cassette for the invention is a DNA molecule of about 5.5 kb, comprising a nucleotide sequence that has at least 95% nucleotide sequence identity to the full length of SEQ ID NO: 1. More preferred is a nucleotide sequence identity of at least 96, 97, 98, or even 99%, in that order of preference.

In an embodiment, the combined single expression cassette for the invention is SEQ ID NO: 1.

As is evident to a skilled person from the composition of the combined single expression cassette for use in the invention, having two heterologous genes in one larger cassette, it is designed and intended for insertion into a single location in the genome of the vector virus.

In an embodiment the rHVT according to the invention is characterised in that the combined single expression cassette as defined for the invention, is inserted in the Us region of the genome of said rHVT in the Us2 gene or in the Us10 gene.

Stable and effective rHVT vectors for the invention could be made by employing the Us2 gene of the HVT genome as the genetic insertion locus for the combined single expression cassette.

In an embodiment the rHVT according to the invention is characterised in that the combined single expression cassette as defined for the invention, is inserted in the Us2 gene.

To facilitate the convenient construction, manipulation, and use of an expression cassette for the invention, this can itself be comprised in a DNA molecule, such as a vehicle allowing cloning or transfection, e.g. such as a plasmid, a Cosmid, a Bacmid, etc., see WO 93/25.665 and EP 996.738.

Examples of common cloning plasmids are e.g. plasmids from the pBR322, or pUC, series. These are widely commercially available.

A plasmid comprising an expression cassette is commonly referred to as a 'transfervector', 'shuttle vector', or 'donor plasmid'. In this situation the plasmid comprises an expression cassette with flanking sequence regions from the target insertion locus of the vector's genome, to direct the insertion.

Typically, a transfervector that is used in transfection is not itself integrated into the genome of the vector, it only facilitates the integration of the expression cassette it carries, e.g. by allowing the insertion to occur by homologous recombination.

In an embodiment of the rHVT according to the invention, the AIV HA gene in the third expression cassette is driven by a promoter from a glycoprotein B (gB) gene from a mammalian herpesvirus.

Therefore in an embodiment the rHVT according to the invention is characterised in that the AIV HA gene is expressed from a third expression cassette comprising in 5' to 3' direction and in this order:

a. a glycoprotein B (gB) gene promoter from a mammalian herpesvirus, b. an AIV HA protein gene, and c. a transcription terminator, and whereby the promoter and the terminator of said expression cassette are operatively linked to the HA gene.

The "gB gene promoter from a mammalian herpesvirus" refers to the promoter that drives the expression of a herpesvirus gB gene, and is situated immediately upstream of that gB gene in a mammalian herpesvirus genome. The gB protein in normal herpesvirus replication is involved in cell-entry and cell-spread. Because the gB gene is such a well-documented and clearly recognisable gene, and because the genomes of many Herpesviridae have been sequenced (in whole or in part), the skilled person can readily identify and obtain such a promoter by routine techniques. Embodiments thereof are disclosed in WO 2012/052384.

A review of herpesvirus gB proteins was presented by Perreira (1994, Infect. Agents Dis., vol. 3, p. 9-28). The promoter of the HSV1 gB gene was studied in detail by Pederson et al. (1992, J. of Virol., vol. 66, p. 6226-6232).

A "mammalian herpesvirus" for the invention relates to a herpesvirus that commonly infects and replicates in a mammalian species. Preferably these viruses are from the taxonomic subfamily of Alphaherpesvirinae. For example: human herpesvirus1 (herpes simplex virus1), bovine herpesvirus1, feline herpes virus1, equine herpesvirus1 (EHV), or pseudorabies virus (PRV, also: suid herpesvirus1). gB gene promoters from such mammalian herpesviruses are advantageously used for the invention.

In an embodiment of the rHVT according to the invention, in the third expression cassette the gB gene promoter from a mammalian herpesvirus for the invention is from PRV, or from EHV. More preferred the gB gene promoter is from PRV.

PRV is also called: suid alphaherpesvirus 1, and the gB gene is also called gII, gp14, or UL27. The first publication of the PRV gB (gII) gene and its promoter, was in 1990, in EP 353809. The use of a PRV gB promoter to drive a heterologous gene in an HVT vector is described in WO 2012/052384.

Such promoters can conveniently be obtained from the prior art, such as from GenBank, for example for:

PRV, from GenBank acc.nr: BK001744, region 20139-19596 (the PRV gB gene is UI 27 or gII), or EHV, from GenBank acc.nr:: AY665713, region 60709-61570 (the EHV1 gB gene is ORF 33).

In addition, the GenBank accession no. pfam00606 conveniently represents a cluster of herpesvirus gB proteins.

To improve the efficacy of the gB gene promoter from a mammalian herpesvirus for the invention even further, while maintaining its stability, the promoter was adapted. The adaptation was an elongation of the promoter sequence, such that now it did not end before the A+1 of the gB gene start codon, but extended downstream of A+1 into the coding region of the gB gene that is normally translated into protein.

A result was that the extended promoter now comprised one or more ATG codons, namely the original start codon and possible other Methionine coding triplets. Such ATG codons, in this position downstream of the TATA box in the promoter could be interpreted by the cellular transcription machinery of the rHVT as a start codon, leading to undesired premature initiation of translation. Therefore ATG codons downstream of the TATA-box of the gB gene promoter, that were now comprised in the extended promoter sequence were modified by mutation to make such ATG's non-functional as a potential start codon. This allowed the gB promoter for the invention to incorporate nucleotides from downstream of the native gB gene start codon and extend into the translated region of the gB gene, however these additional nucleotides are not capable of being translated, but act as an extended leader sequence.

Consequently, gB gene promoter sequences were constructed that contained nucleotides from the gB coding region downstream of the original start codon.

Therefore, in a more preferred embodiment the gB gene promoter from a mammalian herpesvirus comprises nucleotide sequences from the translated region of said gB gene, wherein any ATG nucleotide sequence was changed.

The 'change' of the ATG nucleotide sequence in the extended PRV gB gene promoter for the invention, is preferably made by mutation. The ATG nucleotide sequence can be changed in principle to any other triplet, as long as this does not reduce the stability in replication, or the expression from the vector construct.

Preferably the change is by a single nucleotide, preferably from ATG to TTG.

Thus, to improve its efficacy, the PRV gB gene promoter for use in the invention may comprise a nucleotide sequence that extends downstream of the native PRV gB gene start codon. In that case, to prevent false starts, any ATG codons in that region of PRV gB were mutated. Preferably the PRV gB gene promoter is extended for 129 nt past A+1.

The number of nucleotides downstream of ATG that are comprised in an extended gB promoter for the invention is at least 10, preferably at least 20, 30, 50, 75 or 100, in that order of preference. In practice, the number of nucleotides downstream of A+1 that are to be incorporated into the extended promoter for the invention, can conveniently be taken as the sequence from A+1 up to—but not including—the next downstream ATG codon. In that case only one ATG sequence (that of the start codon) needs to be changed by mutation.

The construct of the third expression cassette as used in the invention, contains a PRV gB gene promoter that was extended for 129 nt past A+1. The only ATG sequence comprised in the extended sequence was from the original start codon, this was changed into TTG by mutation. This cassette showed a similar efficacy and stability in vitro as did the unadapted PRV gB gene promoter, however with a much improved efficacy in vivo.

In an embodiment of the rHVT according to the invention, in the third expression cassette for the invention the PRV gB gene promoter for the invention is a DNA molecule of about 0.7 kb, comprising a nucleotide sequence that has at least 95% nucleotide sequence identity to the full length of the region of nucleotides 20-701 of SEQ ID NO: 2. More preferred is a nucleotide sequence identity of at least 96, 97, 98, or even 99%, in that order of preference.

In an embodiment of the rHVT according to the invention, in the third expression cassette for the invention the PRV gB gene promoter corresponds to nucleotides 20-701 of SEQ ID NO: 2.

In an embodiment of the rHVT according to the invention, the HA protein gene is from an avian influenza A virus.

The AIV serotypes that are currently most relevant to poultry health are serotypes H5, H7, and H9: H5 and H7 because these can be associated with a highly pathogenic pathotype which may even have zoonotic capacity; H9 because this is the most prevalent serotype worldwide, in particular in Middle Eastern- and Asian regions.

Therefore, in an embodiment of the rHVT according to the invention, the AIV HA protein gene encodes an HA protein of a serotype selected from H5, H7 and H9.

The determination whether a HA protein is of a particular serotype can readily be done, e.g. using standard antisera that are available from an international reference laboratory for AIV, a list of which is published by the WHO.

In a preferred embodiment of the rHVT according to the invention, the AIV HA gene is a codon optimised HP AIV HA gene of serotype H5 or H7 as disclosed in WO 2012/052384 SEQ ID NO's: 3 and 5.

The specific HA H9 gene sequence used for the invention was a synthetic sequence, based on a consensus from published HA H9 sequences of recent AIV isolates.

In addition, to further improve the efficacy of the rHVT vector according to the invention in a vaccine for poultry, the HA gene comprised in this vector can be subjected to codon optimisation. The process of codon optimisation is well-known in the art, and involves the adaptation of a nucleotide sequence to encode the intended amino acids, but by way of a nucleotide sequence that employs the codon preference of the (micro-organism) that is used for expressing that gene. Consequently the mutations are essentially silent. This improves the level at which the coding sequence is expressed in a context that differs from that of the origin of the expressed gene.

For the invention, the coding sequence of the AIV HA gene used in the invention was optimised for expression according to the codon preference of HVT.

In an embodiment of the rHVT according to the invention, in the third expression cassette for the invention the AIV HA gene for the invention is a DNA molecule of about 1.7 kb, comprising a nucleotide sequence that has at least 90% nucleotide sequence identity to the full length of the region of nucleotides 713-2395 of SEQ ID NO: 2. More preferred is a nucleotide sequence identity of at least 96, 97, 98, or even 99%, in that order of preference.

In an embodiment of the rHVT according to the invention, in the third expression cassette for the invention the AIV HA gene corresponds to nucleotides 713-2395 of SEQ ID NO: 2.

In an embodiment of the rHVT according to the invention, in the third expression cassette the transcription terminator is derived from FHV1, preferably from the FHV1 Us9 gene. FHV1 Us genes are for example disclosed in GenBank accession number D42113.

In an embodiment of the rHVT according to the invention, in the third expression cassette the transcription terminator is derived from the FHV1 Us9 gene and is about 0.05 kb in size, and comprises a nucleotide sequence that has at least 95% nucleotide sequence identity to the full length of the region of nucleotides 2404-2458 of SEQ ID NO: 2. More preferred is a nucleotide sequence identity of at least 96, 97, 98, or even 99%, in that order of preference.

In an embodiment, the transcription terminator from the FHV1 Us9 gene is the region of nucleotides 2404-2458 of SEQ ID NO: 2.

In a preferred embodiment, the third expression cassette is a cassette as disclosed in WO 2012/052384.

More preferably the third expression cassette is the cassette as employed in the rHVT construct described in WO 2012/052384 as HVP310.

In an embodiment of the rHVT according to the invention, the third expression cassette for the invention comprises an extended gB gene promoter from PRV, and a codon-optimised AIV HA gene, of H9 serotype.

As described above for the first and second expression cassettes, in the third expression cassette its promoter and terminator are 'operatively linked' to the AIV HA gene.

TABLE 2

| | | |
|---|---|---|
| Elements of SEQ ID NO: 2 | | |
| Nucleotide region | | Elements of SEQ ID NO: 2 |
| 20 | 701 | PRV gB gene promoter, extended to nt + 129 |
| 713 | 2395 | AIV HA H9 gene, synthetic and codon optimised |
| 2404 | 2458 | FHV1 Us9 gene transcription terminator |

In nature, the AIV HA protein is expressed as an HA0 (HA zero) protein, which is cleaved post-translationally by proteases that occur in the tissues where AIV replicates. This also activates the AIV's infectivity. The resulting HA1 and HA2 proteins interact to form a heterodimer, whereby HA1 is the 'head' part, and HA2 is the 'stem' part.

In SEQ ID NO: 2, the HA1 region of the HA gene is formed by nucleotides 713-1660, and the HA2 region is formed by nucleotides 1661-2395.

In an embodiment of the rHVT according to the invention, the AIV HA protein gene encodes an HA1 or an HA2 subunit protein.

As HA2 has been reported to be able to induce a broad cross-protective immune response (see Chiu et al., 2013, Ann. NY Acad. Sci., vol. 1283, p. 13-21), therefore in a preferred embodiment, the AIV HA protein gene encodes an HA2 subunit protein.

In an embodiment of the rHVT according to the invention, in the third expression cassette for the invention the AIV HA gene for the invention encodes the HA2 part of the HA protein, and is a DNA molecule of about 0.75 kb, comprising a nucleotide sequence that has at least 90% nucleotide sequence identity to the full length of the region of nucleotides 1661-2395 of SEQ ID NO: 2. More preferred is a nucleotide sequence identity of at least 96, 97, 98, or even 99%, in that order of preference.

In an embodiment of the rHVT according to the invention, in the third expression cassette for the invention the AIV HA gene corresponds to nucleotides 1661-2395 of SEQ ID NO: 2.

The rHVT according to the invention is preferably based on a parental HVT that is an established HVT vaccine strain that replicates well, and is known to be suitable for inoculation of young birds or bird embryos in ovo; for example the HVT vaccine strains PB1 or FC-126. These are generally available: FC-126 from ATCC: VR #584-C, and PB1 is commercially available as live vaccine in frozen infected cells, e.g. from MSD Animal Health.

The incorporation of the first, second, and third expression cassettes, and/or of the combined single expression cassette, all as defined herein for the invention, do not increase the virulence or pathogenicity of the parental HVT (on the contrary), and no reversion to virulence is to be expected, as HVT are naturally apathogenic.

Therefore, in an embodiment the parental HVT used for generation of the rHVT according to the invention is an HVT vaccine strain; preferably an HVT vaccine strain of the PB1- or the FC-126 strain.

The rHVT according to the invention is a live recombinant carrier micro-organism, or a "vector" virus, which can advantageously be used for vaccination of poultry. It combines the features of being a safe and effective vaccine against Marek's disease (MD), and one or more or all of: infectious bursal disease (IBD), Newcastle disease (ND), and avian influenza (AI), and in addition is genetically stable.

Being "genetically stable" for the invention means that the genetic make-up of the rHVT according to the invention does not change in subsequent rounds of virus replication. In the alternative, unstable constructs can lead to the loss of expression of one or more of the inserted heterologous gene(s). This stability can conveniently be monitored with routine techniques, e.g. by subjecting the rHVT according to the invention to subsequent passaging in cell culture. Virus re-isolated during these steps, can be plated on cell culture dishes, covered with agar, and incubated until HVT-specific plaques become visible; all using routine techniques. Next the plaques can be stained for expression of the VP2, F, or the HA protein using suitable antibody preparations in an immunofluorescence assay (IFA) protocol, and adequate positive and negative controls. Any plaques that do no longer show fluorescence can then be recorded, whereby preferably at least 100 individual plaques of a particular rHVT sample should be monitored.

It was surprisingly found that the rHVT according to the invention maintained the presence and the expression of each of the VP2, F, and HA protein genes, in all of the plaques tested, even after 16 consecutive cell-culture passages, and through several weeks of replication in vivo. Details are described in the Examples.

This is a strong and highly significant improvement over alleged multivalent HVT vector constructs described in the prior art.

Also, considering that all of VP2, F, and HA have already been employed as inserts in effective HVT vector vaccines, the fact that they are stably maintained and expressed is also credible proof that the rHVT according to the invention will induce a protective immune response in poultry against these antigens, as well as against MDV, and thus will be an effective quadrivalent vector vaccine.

The rHVT according to the invention can be amplified by common techniques, mainly by replication in vitro, e.g. in cultures of chicken cells, typically primary chicken embryo fibroblast cells (CEF's). These can be prepared by trypsinisation of chicken embryos, all well-known in the art. The CEF's are plated in monolayers and infected with the HVT. This process can be scaled up to industrial size production.

Commonly the rHVT is collected by harvesting the infected host cells that contain the rHVT in a cell-associated form. These cells are taken up in an appropriate carrier composition to provide stabilisation during freezing and storage. Next the infected cells are commonly filled into glass ampoules, which are sealed, frozen and stored in liquid nitrogen. Upon use for vacination, the ampoules are thawed, and the infected cells are taken up into a suitable dilution buffer for in-use stabilisation. In a preferred embodiment, the dilution buffer is a buffer as disclosed in WO 2019/121888.

Although cell-associated frozen storage of HVT is preferred, in situations where use of liquid nitrogen is not feasible, an alternative is to use freeze-drying: this employs the favourable characteristic of HVT that it can be isolated from its host cell by cell-disruption, e.g. by French press or sonifier, using the whole culture. This can be clarified by centrifugation, and is then taken up into a stabiliser, and freeze dried for prolonged storage.

Therefore, in a further aspect, the invention relates to a host cell comprising the rHVT according to the invention.

A "host cell" for the invention, is a cell that is susceptible to infection and replication by an HVT. Examples of such cells are avian cells, and in particular lymphocytes, or fibroblasts.

In an embodiment, the host cell according to the invention is a primary avian cell kept in vitro; i.e. a cell that is derived directly from a non-human animal tissue or -organ, and not from an immortalised cell-line. Typically primary cells can only perform a small and limited number of cell-divisions.

In an embodiment the primary avian host cell for the invention is a primary chicken embryo fibroblast (CEF) kept in vitro.

In an embodiment, the host cell according to the invention is an immortalised avian cell kept in vitro. Several immortalised avian cell-lines have been described, for example in WO 97/044443 and WO 98/006824.

In a preferred embodiment the immortalised avian host cell according to the invention is an immortalised CEF kept in vitro; preferably an immortalised CEF as disclosed in WO 2016/087560.

By different methods of cloning and transfection, the first, second, third, and/or combined single expression cassettes for the invention can be used to obtain the rHVT according to the invention, stably comprising and expressing the expression cassettes in its genome as described herein.

Therefore, a further aspect of the invention relates to a method for the construction of the rHVT according to the invention, said method comprising the insertion of the first, second, third, and/or combined single expression cassettes for the invention, into a region of the genome of an HVT as described for the invention.

The insertion of an expression cassette according to the invention into an HVT genome to generate the rHVT according to the invention, can be performed in different ways, all known in the art. One convenient way is to use a transfervector and the technique of homologous recombination.

Alternatively the rHVT according to the invention can be generated using the CRISPR/Cas9 technology; for example as described by Tang et al, 2018 (Vaccine, vol. 36, p. 716-722).

In particular an rHVT-VP2-F vector virus can be used as is available since 2017 in the commercial vaccine Innovax ND-IBD. This can be further manipulated by inserting the third expression cassette as described herein into the UL 40-41 or the UL44-45 locus of the genome of the rHVT as described herein, using the CRISPR/Cas9 technology. The specific guide RNA sequences that can be used to aim these insertions to these loci are described in the Examples.

As described, the main advantageous use of the rHVT according to the invention is in a vaccine for poultry, providing a safe, stable and effective vaccination against MD, IBD, ND and/or AI or associated signs of disease, and can be administered to poultry at a very young age.

Therefore, a further aspect of the invention relates to the rHVT according to the invention, and/or to the host cell according to the invention, for use in a vaccine for poultry.

The different aspects and embodiments of 'use in a vaccine' of the rHVT according to the invention have been outlined above, and comprise the use as cell-free or as cell-associated virus in a vaccine composition for inoculation of poultry.

Also, in a further aspect the invention relates to a vaccine for poultry comprising the rHVT according to the invention, and/or to the host cell according to the invention, and a pharmaceutically acceptable carrier.

A "vaccine" is well-known to be a composition comprising an immunologically active compound, in a pharmaceutically acceptable carrier. The 'immunologically active compound', or 'antigen' is a molecule that is recognised by the immune system of the inoculated target and induces a protective immunological response from the humoral- and/or the cellular immune system of the target.

The vaccine according to the invention provides protection of chickens against infection and/or disease caused by MDV, IBDV, NDV and/or AIV. This effect is obtained by preventing or reducing the establishment or the proliferation of a productive infection by one or more of these viruses, in their respective target organs. This is achieved for example by reducing the viral load or shortening the duration of the viral replication. In turn this leads to a reduction in the target animal of the number, the intensity, or the severity of lesions and associated clinical signs of disease caused by the viral infection.

However, depending on the virulence of the MDV, IBDV, NDV or AIV field virus that is prevalent in a certain poultry farm or in a certain area, it may be necessary to add a further vaccine component of one or more of these viruses, to assure effective vaccination even to the most pathogenic variants of these viruses. This is all well-known in the art.

The determination of the effectiveness of a vaccine for poultry according to the invention, is well within the skills of the routine practitioner, and can be done for instance by monitoring the immunological response following vaccination or by testing the appearance of clinical symptoms or mortality after a challenge infection, e.g. by monitoring the targets' signs of disease, clinical scores, serological parameters, or by re-isolation of the challenge pathogen, and comparing these results to a vaccination-challenge response seen in mock vaccinated animals. Different ways to assess each of the four virus-infections are well-known in the art.

The protection against MD, IBD, ND and AI induced by the vaccine or by the vaccination according to the invention, results in the vaccinated targets in an improvement of health and economic performance. This can for instance be assessed from parameters such as increased survival, growth rate, feed conversion, and egg-production, as well as reduced costs for health care.

Various embodiments, preferences and examples of a vaccine according to the invention will be outlined below.

The term "poultry" for the invention relates to a species of bird of relevance to veterinary practice, and that is susceptible to inoculation with HVT; the preferred poultry species are: chicken, turkey, and quail. Chickens are the most preferred species.

For the invention, the poultry may be of any type, breed, or variety, such as: layers, breeders, broilers, combination breeds, or parental lines of any of such breeds. Preferred types are: broiler, breeder, and layer. Most preferred are broiler and layer chickens.

A "pharmaceutically acceptable carrier" is intended to aid in the stabilisation and administration of the vaccine, while being harmless and well-tolerated by the target. Such a carrier can for instance be sterile water or a sterile physiological salt solution. In a more complex form the carrier can e.g. be a buffer, which can comprise further additives, such as stabilisers or conservatives. Details and examples are for instance described in well-known handbooks such as: "Remington: the science and practice of pharmacy" (2000, Lippincott, USA, ISBN: 683306472), and: "Veterinary vaccinology" (P. Pastoret et al. ed., 1997, Elsevier, Amsterdam, ISBN 0444819681).

For the present invention, when the vaccine is in the form of cell-associated HVT, then the pharmaceutically acceptable carrier is preferably a mixture of culture medium, about 10% serum, and about 6% DMSO. This carrier also provides for the stabilisation of the rHVT-infected host cells during freezing and frozen storage. The serum can be any serum routinely used for cell culturing such as foetal- or new-born calf serum.

The vaccine according to the invention is prepared from an rHVT according to the invention by methods as described herein, which are readily applicable by a person skilled in the art. For example, the rHVT according to the invention is constructed by insertion of the expression cassettes as described for the invention by transfection and recombination. Next the desired rHVT is selected, and is amplified industrially in smaller or larger volumes, preferably in in vitro cell cultures, e.g. in CEF's. From such cultures a suspension comprising the virus is harvested, either as whole infected cells or as a cell-free preparation obtained by cell-disruption. This suspension is formulated into a vaccine and the final product is packaged. Cell-associated vaccine is then stored in liquid nitrogen and freeze-dried vaccine at −20 or at +4° C.

General techniques and considerations that apply to the manufacture of vaccines under well-known standards for pharmaceutical production are described for instance in governmental directives and regulations (Pharmacopoeia, 9CFR) and in well-known handbooks ("Veterinary vaccinology" and: "Remington", both supra). Commonly such vaccines are prepared sterile, and are prepared using excipients of pharmaceutical quality grade.

Such preparations will incorporate microbiological tests for sterility, and absence of extraneous agents; and may include studies in vivo or in vitro for confirming efficacy and safety. After completion of the testing for quality, quantity, sterility, safety and efficacy, the vaccine can be released for sale. All these are well-known to a skilled person.

In an embodiment the vaccine according to the invention is a cell-associated vaccine.

"Cell-associated" means that the rHVT according to the invention is comprised in host cells according to the invention. Consequently a vaccine of this type comprises both the host cells as well as the rHVT, both according to the invention.

The target animal for the vaccine according to the invention can in principle be healthy or diseased, and may be positive or negative for presence of MDV, IBDV, NDV or AIV, or for antibodies against MDV, IBDV, NDV or AIV. Also the target can be of any weight, sex, or age at which it is susceptible to the vaccination. However it is evidently favourable to vaccinate healthy, uninfected targets, and to vaccinate as early as possible to prevent any field infection and its consequences.

A vaccine according to the invention can thus be used either as a prophylactic- or as a therapeutic treatment, or both, as it interferes both with the establishment and with the progression of an infection by MDV, IBDV, NDV or AIV.

In that respect, a further advantageous effect of the reduction of viral load by the vaccine according to the invention, is the prevention or reduction of shedding and thereby the spread of field virus, both vertically to offspring, and horizontally within a flock or population, and within a geographical area. Consequently, the use of a vaccine according to the invention leads to a reduction of the prevalence of MDV, IBDV, NDV or AIV.

Therefore further aspects of the invention are:

the use of a vaccine according to the invention for reducing the prevalence of MDV, IBDV, NDV or AIV in a population or in a geographical area, and the vaccine according to the invention for reducing the prevalence of MDV, IBDV, NDV or AIV in a population or in a geographical area.

The vaccine according to the invention already provides a multivalent immunity: against IBD, ND, and AI by the expression of the heterologous inserts, and in addition against MD by the HVT vector itself.

Nevertheless it can be advantageous to make further combinations with additional immunoactive components. This can serve to enhance the immune protection already provided, or to expand it to other pathogens.

Therefore, in an embodiment, the vaccine according to the invention is comprising at least one additional immunoactive component.

Such an "additional immunoactive component" may be an antigen, an immune enhancing substance, a cytokine, a further vaccine, or any combination thereof. This provides advantages in terms of cost, efficiency and animal welfare. Alternatively, the vaccine according to the invention, may itself be added to a vaccine.

In an embodiment the at least one additional immunoactive component is an immunostimulatory compound; preferably a cytokine or an immunostimulatory oligodeoxynucleotide.

The immunostimulatory oligodeoxynucleotide is preferably an immunostimulatory non-methylated CpG-containing oligodeoxynucleotide (INO). A preferred INO is an avian Toll-like receptor (TLR) 21 agonist, such as described in WO 2012/089.800 (X4 family), WO 2012/160.183 (X43 family), or WO 2012/160.184 (X23 family).

In an embodiment the at least one additional immunoactive component is an antigen which is derived from a micro-organism pathogenic to poultry. This antigen can be 'derived' in any suitable way, for instance as a 'live' attenuated, an inactivated, or a subunit antigen from that micro-organism pathogenic to poultry.

The additional antigen derived from a micro-organism pathogenic to poultry, is preferably derived from one or more micro-organisms selected from the following groups consisting of:

viruses: infectious bronchitis virus, NDV, Adenovirus, AIV, Egg drop syndrome virus, IBDV, chicken anaemia virus, avian encephalo-myelitis virus, fowl pox virus, turkey rhinotracheitis virus, duck plague virus (duck viral enteritis), pigeon pox virus, MDV, avian leucosis virus, ILTV, avian pneumovirus, and Reovirus;

bacteria: *Escherichia coli, Salmonella, Ornitobacterium rhinotracheale, Haemophilus paragallinarum, Pasteurella multocida, Erysipelothrix rhusiopathiae, Erysipelas, Mycoplasma*, and *Clostridium;* parasites: *Eimeria*; and fungi: *Aspergillus*.

The additional antigen may also be a further vector vaccine, e.g. based on HVT, on MDV2, on NDV, etcetera.

In an embodiment of the vaccine according to the invention, the additional antigen derived from a micro-organism pathogenic to poultry is a 'live' attenuated MDV, IBDV or NDV vaccine strain. This serves to improve and expand the immunogenicity of the vaccine according to the invention, and this is advantageous in those cases or geographic areas where very virulent field strains of MDV, IBDV or NDV are prevalent.

In this regard, the combination of an HVT with an MDV1, MDV2, or HVT is known; for the invention an MDV of strain Rispens (MDV1), strain SB1 (MDV2), or strains FC-126 or PB1 (HVT) is preferred as additional immunoactive component.

To improve the response against ND, the rHVT according to the invention may be combined with an NDV vaccine strain such as the mild live NDV vaccine strain C2.

Similarly, to improve the response against IBD, the rHVT according to the invention may be combined with a live IBDV vaccine strains such as D78, PBG98, Cu-1, ST-12 or 89-03.

As the skilled person will appreciate, these 'combinations' also include vaccination schedules wherein the rHVT according to the invention and the additional immunoactive component are not applied simultaneous, but concurrent or sequential; e.g. the rHVT may be applied in ovo, the NDV C2 at day one, and the IBDV 89-03 at day 17.

Therefore, in an embodiment of the vaccine according to the invention comprising at least one additional immunoactive component, the at least one additional immunoactive component is a micro-organism selected from the group consisting of a vaccine strain from: MDV, IBDV, NDV, or AIV, or any combination thereof.

More preferably the additional immunoactive component is one or more selected from the group consisting of: MDV Rispens, MDV SB1, NDV C2, IBDV D78 and IBDV 89-03.

A vaccine according to the invention can be prepared by methods as described and exemplified herein.

Therefore, a further aspect of the invention relates to a method for the preparation of the vaccine for poultry according to the invention, said method comprising the steps of:

a. infecting host cells in vitro with the rHVT according to the invention, b. harvesting the infected host cells, and c. admixing the harvested infected host cells with a pharmaceutically acceptable carrier.

Suitable host cells and pharmaceutically acceptable carriers for the invention have been described above. Also, suitable in vitro methods for infection, culture and harvesting are well-known in the art and are described and exemplified herein.

Consequently, the different aspects and embodiments of the invention can advantageously be used to produce a safe, stable and effective vaccine for poultry.

Therefore, in a further aspect, the invention relates to the use of the rHVT, or the host cell according to the invention, or any combination thereof, for the manufacture of a vaccine for poultry.

It goes without saying that admixing other compounds, such as stabilisers, carriers, adjuvants, diluents, emulsions, and the like to vaccines according to the invention are also within the scope of the invention. Such additives are described in well-known handbooks such as: "Remington", and "Veterinary Vaccinology" (both supra).

This way the efficacy of a vaccine according to the invention, to protect poultry with a single inoculation at very young age against MD, IBD, ND and AI can be further optimised when needed.

A vaccine according to the invention can be prepared in a form that is suitable for administration to a poultry target, and that matches with a desired route of application, and with the desired effect.

Depending on the route of application of the vaccine according to the invention, it may be necessary to adapt the vaccine's composition. This is well within the capabilities of a skilled person, and generally involves the fine-tuning of the efficacy or the safety of the vaccine. This can be done by adapting the vaccine dose, quantity, frequency, route, by using the vaccine in another form or formulation, or by adapting the other constituents of the vaccine (e.g. a stabiliser or an adjuvant).

The vaccine according to the invention in principle can be given to target poultry by different routes of application, and at different points in their lifetime, provided the inoculated rHVT can establish a protective infection.

However, because an infection with MDV, IBDV, NDV, or AIV can be established already at very young age, it is advantageous to apply the vaccine according to the invention as early as possible. Therefore the vaccine according to the invention can be e.g. applied at the day of hatch ("day 1"), or in ovo, e.g. at 18 days of embryonic development, all well-known in the art.

Therefore, in an embodiment, the vaccine according to the invention is administered to poultry in ovo.

Equipment for automated injection of a vaccine into a fertilized egg at industrial scale, is available commercially. This provides the earliest possible protection, while minimising labour cost. Different in ovo inoculation routes are known, such as into the yolk sac, the embryo, or the allantoic fluid cavity; these can be optimised as required. Preferably in ovo inoculation with an HVT is performed such that the needle touches the embryo.

Preferably a vaccine according to the invention is formulated as an injectable liquid, suitable for injection, either in ovo, or parenteral; for example as: a suspension, solution, dispersion, or emulsion.

In an embodiment, the vaccine according to the invention is administered by parenteral route. Preferably by intramuscular- or subcutaneous route.

The exact amount of rHVT according to the invention per animal dose of the vaccine according to the invention is not as critical as it would be for an inactivated type vaccine; this because the rHVT will replicate in the target animal up to a level of viraemia that is biologically sustainable. In principle the vaccine dose only needs to be sufficient to initiate such a productive infection. A higher inoculum dose hardly shortens the time it takes to reach an optimal viraemic infection in the host. Therefore, very high doses are not more effective and in addition are not attractive for economic reasons.

A preferred inoculum dose is therefore between $1 \times 10^{\wedge}1$ and $1 \times 10^{\wedge}5$ plaque forming units (pfu) of rHVT according to the invention per animal dose, more preferably between $1 \times 10^{\wedge}2$ and $1 \times 10^{\wedge}4$ pfu/dose, even more preferably between 500 and 5000 pfu/dose; most preferably between about 1000 and about 3000 pfu/dose.

When the vaccine according to the invention is cell-associated, these amounts of rHVT are comprised in infected host cells.

Methods to count viral particles of the rHVT according to the invention are well-known.

The volume per animal dose of the rHVT according to the invention can be optimised according to the intended route of application: in ovo inoculation is commonly applied with a dose of between about 0.01 and about 0.5 ml/egg, and parenteral injection is commonly done with a dose of between about 0.1 and about 1 ml/bird.

Determination of what is an immunologically effective amount of the vaccine according to the invention, or the optimisation of the vaccine's volume per dose, are both well within the capabilities of the skilled artisan.

The dosing regimen for applying the vaccine according to the invention to a target organism can be in single or multiple doses, in a manner compatible with the formulation of the vaccine, and in such an amount as will be immunologically effective.

Preferably, the regimen for the administration of a vaccine according to the invention is integrated into existing vaccination schedules of other vaccines that the target poultry may require, in order to reduce stress to the animals and to reduce labour costs. These other vaccines can be administered in a simultaneous, concurrent or sequential fashion, in a manner compatible with their licensed use.

As described above, and as exemplified hereinafter, the vaccine according to the invention can advantageously be used to prevent or reduce infection by one, or more, or all of MDV, IBDV, NDV, and AIV, and the prevention or reduction of the (signs of) disease associated with such infections, by a single inoculation at very young age.

Therefore further aspects of the invention are:

the use of the vaccine according to the invention, for preventing or reducing infection by MDV, IBDV, NDV, and/or AIV, or their associated signs of disease.

a method for preventing or reducing infection by MDV, IBDV, NDV, and/or AIV, or their associated signs of disease, the method comprising the administration of the vaccine according to the invention to poultry.

a method of vaccination of poultry to prevent or reduce infection by MDV, IBDV, NDV, and/or AIV, or their associated signs of disease, the method comprising the step of inoculating said poultry with the vaccine according to the invention.

Details on the use of the vaccine according to the invention, by inoculation of poultry have been described above; specifically the inoculation by intramuscular or subcutaneous inoculation of day old chicks, and the in ovo inoculation of 18 day old embryos.

The invention will now be further described with reference to the following, non-limiting, examples.

EXAMPLES

Example 1: Construction and Testing of Multivalent rHVT Vectors 1.1. Constructs Made and Tested Based on the HVT vector construct HVP360 (WO 2016/102647), a series of HVT recombinants were made that additionally expressed an AIV HA gene. HVP360 expresses the NDV-F and the IBDV-VP2 genes from the Us2 locus. Using the CRISPR/Cas9 technique as described by Tang et al. 2018 (supra), an extra cassette expressing AIV-HA H9, was introduced into the UL region of the HVP360 genome, at different sites. Several constructs were made with insertion of the HA gene expression cassette, and four constructs were assessed in more detail; insertion sites are indicated relative to GenBank accession number AF291866:

HVP400: HA gene inserted between UL40 and UL41 of HVP360, between nt. 88054-88055

HVP401: HA between UL44 and UL45, between nt. 94482-94483

HVP402: HA between UL47 and UL48, between nt. 99588-99589

HVP403: HA between UL54 and LORF4, between nt: 110395-110396.

The guide RNA sequences used for the CRISPR/Cas9 directed insertions are:

```
insertion between UL40 and UL41:
                            (SEQ ID NO: 3)
5'-ACCTAAAGTACACGTGAATC-3' insertion between UL44 and UL45:
                            (SEQ ID NO: 4)
5'-ACATCGGGACGTACATCATG-3' insertion between UL47 and UL48:
                            (SEQ ID NO: 5)
5'-TGGCGGTTACAATTTCCACG-3' insertion between UL54 and LORF4:
                            (SEQ ID NO: 6)
5'-TTAGATTTCCGGACAGCCTG-3'.
```

NB: the SEQ ID numbers 3-6 are indicated here in DNA code, as they were inserted into a DNA plasmid, and were then transcribed to produce the guide RNA's.

The guide RNA's were designed using the Internet website: zlab.bio/guide-design-resources.

1.2. Genetic Stability In Vitro

These four rHVT vector constructs were passaged on CEF cells in vitro 16 times. P16 plaques were monitored for the expression of the inserted genes by IFA as follows: overnight established CEF monolayers were infected with one of the 4 HVT recombinants at 16th passage level. Plates were incubated for 2-3 days until CPE was clearly visible, and then fixated with 96% ethanol. Expression of IBDV-VP2, NDV-F or AIV-H9 was detected with monoclonal antibodies specific for each of the antigens as first reagent, and an Alexa™ labelled conjugate as secondary antibody. Next plates were read by UV microscopy. About 100 plaques were counted for each of the recombinants to assess expression. All plaques tested for HVP400 and HVP401 showed full expression of the VP2, F and HA genes. This confirmed functional and stable expression of the three genes up to (at least) cell passage level 16. Plaques tested for HVP402 and HVP403 showed minor loss of expression for VP2 and/or of the F. This is outlined in Table 3.

TABLE 3

Expression of heterologous genes in rHVT at cell-passage level 16

| Isolate | Expression of antigen by IFA | | |
|---------|------|------|------|
|  | VP2 | F | HA |
| HVP400 | 100% | 100% | 100% |
| HVP401 | 100% | 100% | 100% |
| HVP402 | 99% | 98% | 100% |
| HVP403 | 100% | 99% | 100% |

Unfortunately even a small instability in the expression of one of the heterologous genes is not acceptable. Under conditions of increased selection-pressure such as the production of large amounts of virus, or the replication for weeks in vivo in a vaccinated target, such a mutant has a replicative advantage and will rapidly outgrow its relatives that do express all heterologous genes. This would lead to a loss of expression in an increasing part of the vector viruses. Consequently, only the constructs showing fully stable expression for all of the heterologous genes, here: HVP400 and HVP401, were acceptable for further vaccine development.

Example 2: Vaccination and In Vivo Passaging 2.1. Introduction

This experiment tested the replication and serological efficacy of rHVT vector constructs HVP400 and HVP401 in chickens, by vaccination of SPF layer chicks, subcutaneously, at 1-day-old. Group size was 12 animals, plus 5 hatchmates.

To determine replication in vivo of the vector vaccines, HVT viremia levels in the spleen (day 11) and peripheral blood lymphocytes (day 32) of vaccinated animals were determined. Blood samples were taken at periodic intervals, so that antibody levels could be determined in the serum using specific serology tests.

2.2. Experimental

HVP400:

rHVT comprising the gB-AIV/HA/H9 insert in intergenic region UL40-41, and having the mIE1-IBDV/VP2+hIE1-NDV/F inserted in Us2. Virus was at 16th cell-passage, and was stored in infected CEF cells in liquid nitrogen. Viral titre (in infected cells) was $1.2 \times 10^{\wedge}6$ pfu/ml.

HVP401 rHVT comprising the gB-AIV/HA/H9 insert in intergenic region UL45-46, and having the mIE1-1BDV/VP2+hIE1-NDV/F inserted in Us2. Virus was at 16th cell-passage, and was stored in infected CEF cells in liquid nitrogen. Viral titre (in infected cells) was $1.0 \times 10^{\wedge}6$ pfu/ml.

Dosing was 0.2 ml/chick, given subcutaneous in the neck, with about 2000 pfu/chick, in standard HVT/CEF diluent.

No acclimatization was applied as the chicks were placed into negative pressure isolators shortly after hatch, and were labelled and vaccinated shortly thereafter.

Blood samples were taken from 5 hatch mates at day 1, these samples were tested serologically, to assure that all animals were negative for antibodies against NDV, IBDV and AIV on the day of vaccination.

Blood samples were taken from the vaccinated chicks on days 14, 21, 28, and 42 after vaccination. Blood samples were collected from the wing vein into tubes with clot activator, and kept at ambient temperature.

Viremia:

Viremia sampling in spleen and peripheral blood lymphocytes (PBL) was done as follows: at day 11 p.v., spleens were isolated post mortem from 5 chicks per group. Clean tweezers were used for each chick.

Spleens were collected in tubes with 5 ml of 10 mM PBS with phenol red indicator and antibiotics, and kept on ice until processing. Next spleens were homogenised, taken up into fresh medium and counted.

Blood samples for testing vireamia in PBL's were collected on day 32 p.v., from a wing vein into heparinised tubes, and kept on ice until processing by centrifugation, taken up into fresh medium, and counting.

For each sample about $2 \times 10^{\wedge}6$ cells were inoculated on pre-established CEF monolayers, and incubated for 3-4 days, after which plates were fixed, and stained by IFA.

Serology

Blood samples for testing of serological responses were centrifuged, serum was collected and complement was inactivated. These samples were used in a variety of tests to determine the seroresponse of the vaccinated chickens against the expressed heterologous genes: IBDV-VP response was measured by virus-neutralisation (VN) assay using classic IBDV virus strain D78; NDV-F response was measured by ELISA and expressed in units relative to standard samples; and AIV-HA response was determined by hemagglutination-inhibition assay using HA H9 antigen.

2.3. Results and Conclusions

Viremia rHVT viremia was detected in spleen and in PBLs at 11 respectively at 32 days post vaccination (dpv). From each rHVT and from each time point, 5 animal isolates were tested. Details of average viremia numbers are presented in Table 4.

TABLE 4

| Results of rHVT vireamia in vivo | | |
|---|---|---|
| | HVT viremia in avg. no. of PFU/2 × 10^6 cells | |
| Vaccine | spleen 11 dpv | PBLs 32 dpv |
| HVP400 | 3 | 2 |
| HVP401 | 10 | 16 |

As is clear from these results: the multivalent rHVTs according to the invention do replicate and disseminate in a target animal. However their replication is relatively slow. Undoubtedly this is a result of carrying and maintaining the expression of the three heterologous gene inserts.

Genetic Stability In Vivo

The rHVT viruses obtained in the viremia assay were tested for continued expression of the heterologous genes. 100 plaques were analysed by IFA, from all 3+2 isolates from spleen and PBLs of HVP400, and from 5 isolates from spleen and 5 from PBLs of HVP401.

In all cases, all plaques analysed of HVP400 and HVP401, after replication in vivo, maintained the expression of all the three heterologous genes: IBDV-VP2, NDV-F, and AIV-HA.

It was concluded that the genetic stability of rHVT constructs HVP400 and HVP401 in vivo was excellent.

Serology

The results of the serological responses induced by the vaccination of chickens with rHVT vectors HVP400 and HVP401 are represented in Table 5. The 'controls' are the hatchmates that were tested at day 1 of the trial.

In nature, the immuneresponse against the pathogens from which the three heterologous antigens were derived: IBDV, NDV, and AIV, all rely to a very large extent on a humoral immune response. Consequently, a measurement of the antibody response generated, is a reliable correlate of in vivo protection against infection.

Therefore, the types of sero-diagnoses applied for detecting the immune response, were selected to measure this protective antibody response. This correlation is self-evident for virus-neutralisation of IBDV and for HI of AIV, as indications of viral capture by specific antibodies. This also applies to the Elisa titres against NDV-F: from the prior art and previous experience, it is known that a titre in this test of above about 1000 Elisa units is protective against an NDV challenge infection.

In addition, as the vector virus for the HVP400 and HVP401 constructs is still a functioning HVT virus, the protective capacity against Marek's disease is inherent and unchanged.

It can therefore be concluded that vaccination with each of rHVT HVP400 or HVP401 induces in target animals a protective immuneresponse against each of IBDV, NDV, AIV and MDV. To confirm this, vaccination-challenge experiments with each of these antigens are underway.

In regard to differences between the constructs HVP400 and HVP401: while HVP400 seemed to be somewhat lower in vireamia than HVP401, nevertheless the serological responses induced by both these vectors is very similar.

TABLE 5

| | Serology results from rHVT vaccination trial | | | | | | | | | | | | | | |
|---|---|---|---|---|---|---|---|---|---|---|---|---|---|---|---|
| | IBDV-VP2 in Log2 VN-D78 at dpv | | | | | NDV-F in ELISA units at dpv | | | | | AIV-HA H9 in Log2 HI at dpv | | | | |
| Vaccine | 1 | 14 | 21 | 28 | 42 | 1 | 14 | 21 | 28 | 42 | 1 | 14 | 21 | 28 | 42 |
| HVP400 | — | 0.0 | 0.0 | 2.0 | 4.0 | — | 100 | 272 | 1781 | 3836 | — | 0.0 | 1.8 | 3.6 | 4.2 |
| HVP401 | — | 0.0 | 1.4 | 2.8 | 7.4 | — | 94 | 366 | 1656 | 2441 | — | 0.6 | 3.2 | 4.2 | 4.2 |
| Controls | 0.0 | — | — | — | — | 109 | — | — | — | — | 0.0 | — | — | — | — |

Example 3: Vaccination-Challenge Experiment

To confirm the protective capacity of the serological response against Avian influenza virus by the recombinant HVT vectors according to the invention, as described in Example 2 above, a vaccination-challenge trial was performed.

3.1. Set-Up

Animals used were one day old chicks, either SPF or MDA+ for H9N2 AIV. These were vaccinated by subcutaneous route essentially as described above, at day old with HVT vector vaccines HVP400 or HVP401 (both groups n=16), which were at 16th cell passage level. The HVT vector vaccine dose was about 800 PFU/chick. Next chicks were given a challenge infection with a heterologous LPAI H9N2 strain; SPF chicks were challenged at 3 weeks p.v., and MDA+ chicks at 6 w. p.v. The challenge virus used was: LPAI A/chicken/Egypt/V1527/2018 (H9N2), which was administered intranasally at $10^{\wedge}6$ EID50, in 0.2 ml.

Negative control was a group (n=16) vaccinated with a non-recombinant HVT, and positive controls (n=11) were vaccinated with a classic inactivated H9N2 vaccine (NOBILIS® INFLUENZA H9N2+ND). 5 SPF hatchmates were tested for serology, to confirm that SPF animals were negative for HA-antibodies. Similarly, 10 MDA+ animals were tested for serology to confirm their MDA+H9 HA status.

From all HVT vaccinated groups 5 chicks were euthanised at 15 d. p.v., to test their spleens for HVT viremia, to confirm HVT vector vaccine take and replication. Choana swabs were taken 1, 3, and 6 days post challenge to monitor the shedding of the challenge virus. At periodic intervals blood samples were taken to measure antibody levels in the serum. Clinical signs were monitored from 1-day post challenge until all chicks in one group were free of AI symptoms.

The daily clinical scoring system used the following points system:

| | |
|---|---|
| 0 | No clinical signs |
| 1 | Mild clinical signs |
| 2 | Moderate clinical signs |
| 3 | Severe clinical signs. |

3.2. Results

The HVT vaccines replicated well: the spleens tested from all HVT vaccinated groups were all positive for vaccine take at day 15. This lasted throughout the experiment: viremia tests on PBLs taken at 42 (SPF) or 63 (MDA+) days p.v., were also all positive for HVT.

To determine the genetic stability of HVP400 and HVP401 vector viruses in vivo, the viremia plaques of viruses from day 15 p.v. were stained with specific antisera against NDV-F, IBDV-VP2 or AIV-HA H9. All plaques showed stable expression of all of the inserted genes. Clearly positive expression of the NDV F-gene and of the IBDV-VP2 genes were also detected by Elisa of serum samples taken at 28, 42 and 63 days p.v., in the groups that received one of the vector vaccines. The negative controls (non-recombinant HVT vaccine) were negative for the heterologous antigens at all timepoints.

AIV serology showed that MDA+ chicks had high anti-HA H9 titers at the start of the experiment, as detected by indirect Elisa and HI test. The MDA+ chicks receiving vector vaccine had clearly positive anti-HA antibodies at day 14 p.v., but these titres dropped off to background levels on days 28 and 42 p.v., similar to mock HVT vaccinated MDA+ chicks. SPF chicks receiving vector vaccine showed increased anti-H9 titers at day 21 p.v.

It is interesting to note that the pre-existence of H9 HA MDA in chicks did not influence the HVT vector vaccines according to the invention, even though these expressed an HA H9 antigen; the vector replication and dissemination in the inoculated chick were good, and so was the expression of the heterologous genes, including that of the H9 HA antigen.

Detection of H9N2 challenge virus replication was done by taking choana swabs at day 1, 3 and 6 after challenge. The swabs were analysed by qPCR using the FLU™ PCR (BioChek). The peak of AIV challenge virus replication was found to be at day 3 p.c. To get an impression of the level of reduction of challenge virus replication induced by the vector vaccines, the qPCR scores for vector vaccinates from that day were compared to the scores from mock HVT vaccinated-challenged chicks. Considering the field situation wherein all chicks are born from AIV vaccinated mothers, and are thus HA-antibody positive, the results of the MDA+ groups are relevant.

The results were as follows: the relative amount of H9N2 challenge virus reisolated at day 3 p.c., measured by qPCR, for the groups of MDA+ chicks was (relative to 100% set for the mock HVT vaccine): 53.2% for the HVP400 vector vaccine; 61.4% for the HVP401 vector vaccine; and 77.7% for the H9N2 inac vaccine. This indicates that the reduction of AIV challenge virus replication by the HVT vector vaccines according to the invention was at least as good, even slightly better, than the reduction by the classic inactivated AIV vaccine.

A similar image emerged from the results of the clinical scores observed after challenge. These were measured up to 3 weeks p.c. but no scores were found after 14 days p.c. Table 6 presents the average clinical scores per day after challenge for the various groups of vaccinated MDA+ chicks, as well as the total of the clinical scores/group over days 1-14 p.c.

Interestingly, the HVT vector vaccines according to the invention prevented clinical signs from the challenge infection better than the classical inac vaccine.

TABLE 6

Average clinical scores after challenge
for the different groups of MDA+ chicks vaccinated

| Chicks | Vaccines | AIV clinical score on day X post challenge | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | Total |
| MDA+ | mock HVT | 0.0 | 0.9 | 0.6 | 0.9 | 0.8 | 0.9 | 0.3 | 0.1 | 0.2 | 0.3 | 0.1 | 0.2 | 0.2 | 0.2 | 5.8 |
| | HVP400 | 0.0 | 0.1 | 0.0 | 0.0 | 0.0 | 0.0 | 0.0 | 0.0 | 0.0 | 0.0 | 0.0 | 0.0 | 0.0 | 0.0 | 0.1 |
| | HVP401 | 0.0 | 0.0 | 0.2 | 0.4 | 0.1 | 0.2 | 0.0 | 0.0 | 0.0 | 0.0 | 0.0 | 0.0 | 0.0 | 0.0 | 0.9 |
| | Inac H9N2 | 0.0 | 0.2 | 0.5 | 0.5 | 0.4 | 0.4 | 0.1 | 0.1 | 0.1 | 0.1 | 0.0 | 0.0 | 0.0 | 0.0 | 2.4 |

3.3. Conclusions:

The HVP400 and HVP401 vector vaccines were genetically stable in vivo at 15 days p.v., and replicated and expressed the 3 heterologous genes well, even in chicks that were MDA+ for one of the expressed antigens. Both vectors induced clear antibody titers in vaccinated chicks, against each of the three heterologous antigens.

Also, infection and disease resulting from a challenge infection with a heterologous LPAI H9N2 virus could be prevented to a large extend: challenge virus replication was reduced, and clinical signs were almost completely prevented.

This is remarkable, as the HA specific antibody levels that were induced in the HVT vector vaccinated MDA+ animals, were relatively low. This suggests that for the immune-protection against AIV infection as induced by the HVT vector vaccines according to the invention, the relevance of a humoral immune response is limited.

---

The invention claimed is:

1. A recombinant herpesvirus of turkeys (rHVT) expressing an infectious bursal disease virus (IBDV) viral protein 2 (VP2) gene and a Newcastle disease virus (NDV) fusion (F) protein gene from a first and a second expression cassette which are inserted in the unique small (Us) region of the genome of said rHVT, wherein the rHVT also expresses an avian influenza virus (AIV) haemagglutinin (HA) gene from a third expression cassette which is inserted in the unique long (UL) region of the genome of said rHVT either between the UL40 and UL41 genes, or between the UL44 and UL45 genes.

2. The rHVT of claim 1, wherein the IBDV VP2 gene is present in the first expression cassette comprising in 5' to 3' direction and in the order of:
   a. a murine cytomegalovirus immediate early 1 gene (mCMV-IE1) promoter,
   b. an IBDV VP2 gene, and
   c. a transcription terminator,
and whereby the promoter and the terminator of said expression cassette are operatively linked to the VP2 gene.

3. The rHVT of claim 1, wherein the NDV F protein gene is present in the second expression cassette comprising in 5' to 3' direction and the order of:
   a. a human cytomegalovirus immediate early 1 gene (hCMV-IE1) promoter,
   b. an NDV F protein gene, and
   c. a transcription terminator,
and whereby the promoter and the terminator of said expression cassette are operatively linked to the F gene.

4. The rHVT of claim 1, wherein the first and the second expression cassette are inserted in the same locus or in different loci of the Us region of the genome of said rHVT.

5. The rHVT of claim 1, wherein the first and the second expression cassette are both inserted in the Us2 gene, or are both inserted in the Us10 gene, or one is inserted in the Us2 gene and the other is inserted in the Us10 gene.

6. The rHVT of claim 1, wherein the first and the second expression cassette are combined into a single expression cassette.

7. The rHVT of claim 6, wherein the combined single expression cassette is inserted in the Us2 gene.

8. The rHVT of claim 1, wherein the AIV HA gene is present in the third expression cassette comprising, in 5' to 3' direction and in the order of:
   a. a glycoprotein B (gB) gene promoter from a mammalian herpesvirus,
   b. an AIV HA protein gene, and
   c. a transcription terminator,
and whereby the promoter and the terminator of said expression cassette are operatively linked to the HA gene.

9. The rHVT of claim 1, wherein the AIV HA protein gene encodes an HA protein of a serotype selected from the group consisting of H5, H7 and H9.

10. A host cell comprising the rHVT of claim 1.

11. A vaccine for poultry comprising the rHVT of claim 1, and a pharmaceutically acceptable carrier.

12. The vaccine of claim 11, further comprising at least one additional immunoactive component.

13. A method of preparing a vaccine for poultry comprising the steps of:
   a. infecting host cells in vitro with the rHVT of claim 1,
   b. harvesting the infected host cells, and
   c. admixing the harvested infected host cells with a pharmaceutically acceptable carrier.

14. A method of preventing or reducing infection by MDV, IBDV NDV and/or AIV, or their associated signs of disease in poultry, comprising administering the vaccine of claim 12 to the poultry.

15. A vaccine for poultry comprising the host cell of claim 10, and a pharmaceutically acceptable carrier.

16. A method of vaccinating poultry to prevent or reduce infection by MDV, IBDV NDV and/or AIV, or their associated signs of disease, comprising the step of inoculating said poultry with the vaccine of claim 15.

17. The rHVT of claim 8, wherein the AIV HA gene encodes an HA protein of a serotype selected from the group consisting of H5, H7 and H9.

18. The rHVT of claim 17, wherein the NDV F protein gene is present in the second expression cassette comprising in 5' to 3' direction and in the order of:
   a. a human cytomegalovirus immediate early 1 gene (hCMV-IE1) promoter,
   b. an NDV F protein gene, and
   c. a transcription terminator,
and whereby the promoter and the terminator of said expression cassette are operatively linked to the F gene.

19. The rHVT of claim 18, wherein the IBDV VP2 gene is present in the first expression cassette comprising in 5' to 3' direction and in this order:
   a. a murine cytomegalovirus immediate early 1 gene (mCMV-IE1) promoter,
   b. an IBDV VP2 gene, and
   c. a transcription terminator,
and whereby the promoter and the terminator of said expression cassette are operatively linked to the VP2 gene.

20. A method of vaccinating poultry to prevent or reduce infection by MDV, IBDV NDV and/or AIV, or their associated signs of disease, comprising the step of inoculating said poultry with the vaccine of claim 19.

* * * * *

SEQUENCE LISTING

```
<160> NUMBER OF SEQ ID NOS: 6

<210> SEQ ID NO 1
<211> LENGTH: 5498
<212> TYPE: DNA
<213> ORGANISM: Artificial Sequence
<220> FEATURE:
<223> OTHER INFORMATION: Combined single expression cassette
<220> FEATURE:
<221> NAME/KEY: promoter
<222> LOCATION: (1)..(1391)
<223> OTHER INFORMATION: murine cytomegalovirus immediate early 1 gene
      promoter-enhancer
<220> FEATURE:
<221> NAME/KEY: gene
<222> LOCATION: (1423)..(2781)
<223> OTHER INFORMATION: IBDV strain F 52/70, VP2 gene
<220> FEATURE:
<221> NAME/KEY: terminator
<222> LOCATION: (2812)..(3021)
<223> OTHER INFORMATION: SV40 polyA signal + terminator
<220> FEATURE:
<221> NAME/KEY: promoter
<222> LOCATION: (3160)..(3520)
<223> OTHER INFORMATION: Human cytomegalovirus immediate early 1 gene
      core promoter
<220> FEATURE:
<221> NAME/KEY: gene
<222> LOCATION: (3545)..(5206)
<223> OTHER INFORMATION: NDV Clone 30 F-gene
<220> FEATURE:
<221> NAME/KEY: terminator
<222> LOCATION: (5218)..(5498)
<223> OTHER INFORMATION: hCMV IE1 gene terminator

<400> SEQUENCE: 1
aactccgccc gttttatgac tagaaccaat agtttttaat gccaaatgca ctgaaatccc      60
ctaatttgca aagccaaacg ccccctatgt gagtaatacg gggacttttt acccaatttc     120
ccaagcggaa agccccctaa tacactcata tggcatatga atcagcacgg tcatgcactc     180
taatggcggc ccatagggac tttccacata gggggcgttc accatttccc agcataggg      240 tggtgactca atggccttta cccaagtaca ttgggtcaat gggaggtaag ccaatggggtt     300 tttcccatta ctggcaagca cactgagtca aatgggactt tccactgggt tttgcccaag     360
tacattgggt caatgggagg tgagccaatg ggaaaaaccc attgctgcca agtacactga     420
ctcaataggg actttccaat gggtttttcc attgttggca agcatataag gtcaatgtgg     480
gtgagtcaat agggactttc cattgtattc tgcccagtac ataaggtcaa tagggggtga     540
atcaacagga aagtcccatt ggagccaagt acactgcgtc aatagggact ttccattggg     600
ttttgcccag tacataaggt caatagggga tgagtcaatg ggaaaaaccc attggagcca     660
agtacactga ctcaataggg actttccatt gggttttgcc cagtacataa ggtcaatagg     720
gggtgagtca acaggaaagt cccattggag ccaagtacat tgagtcaata gggactttcc     780
aatgggtttt gcccagtaca taaggtcaat gggaggtaag ccaatgggtt tttcccatta     840
ctggcacgta tactgagtca ttagggactt ccaatgggt tttgcccagt acataaggtc     900
```

-continued

```
aatagggtg aatcaacagg aaagtcccat tggagccaag tacactgagt caatagggac      960
tttccattgg gttttgccca gtacaaaagg tcaataggg gtgagtcaat gggttttcc       1020 cattattggc acgtacataa ggtcaatagg ggtgagtcat tgggtttttc cagccaattt     1080
aattaaaacg ccatgtactt tcccaccatt gacgtcaatg ggctattgaa actaatgcaa      1140
cgtgaccttt aaacggtact ttcccatagc tgattaatgg gaaagtaccg ttctcgagcc      1200
aatacacgtc aatgggaagt gaaagggcag ccaaaacgta acaccgcccc ggttttcccc      1260
tggaaattcc atattggcac gcattctatt ggctgagctg cgttctacgt gggtataaga      1320
ggcgcgacca gcgtcggtac cgtcgcagtc ttcggtctga ccaccgtaga acgcagagct      1380
cctcgctgca ggcggccgct ctagaactcg tcgatcgcag cgatgacaaa cctgcaagat      1440
caaacccaac agattgttcc gttcatacgg agccttctga tgccaacaac cggaccggcg      1500
tccattccgg acgacaccct ggagaagcac actctcaggt cagagacctc gacctacaat      1560
ttgactgtgg gggacacagg gtcagggcta attgtctttt tccctggatt ccctggctca      1620
attgtgggtg ctcactacac actgcagagc aatgggaact acaagttcga tcagatgctc      1680
ctgactgccc agaacctacc ggccagctac aactactgca gactagtgag tcggagtctc      1740
acagtgaggt caagcacact ccctggtggc gtttatgcac taaacggcac cataaacgcc      1800
gtgaccttcc aaggaagcct gagtgaactg acagatgtta gctacaatgg gttgatgtct      1860
gcaacagcca acatcaacga caaaattggg aatgtcctgg taggggaagg ggtcactgtc      1920
ctcagcctac ccacatcata tgatcttggg tatgtgaggc ttggtgaccc cattcccgct      1980
atagggcttg acccaaaaat ggtagctaca tgcgacagca gtgacaggcc cagagtctac      2040
accataactg cagccgatga ttaccaattc tcatcacagt accaaccagg tggggtaaca      2100
atcacactgt tctcagccaa cattgatgct atcacaagcc tcagcattgg gggagagctc      2160
gtgtttcaaa caagcgtcca aggccttgta ctgggcgcca ccatctacct tataggcttt      2220
gatgggactg cggtaatcac cagagctgta gccgcagata atgggctgac ggccggcacc      2280
gacaatctta tgccattcaa tcttgtcatt ccaaccaatg agataaccca gccaatcaca      2340
tccatcaaac tggagatagt gacctccaaa agtggtggtc aggcagggga tcagatgtca      2400
tggtcggcaa gtgggagcct agcagtgacg atccatggtg caactatcc aggggccctc       2460 cgtcccgtca cactagtagc ctacgaaaga gtggcaacag gatccgtcgt tacggtcgct      2520
ggggtgagta acttcgagct gattccaaat cctgaactag caaagaacct ggttacagaa      2580 tacgccgat ttgacccagg agccatgaac tacacaaaat tgatactgag tgagagggac       2640
cgtcttggca tcaagaccgt ctggccaaca agggagtaca ctgattttcg tgagtacttc      2700
atggaggtgg ccgacctcaa ctctcccctg aagattgcag gagcatttgg cttcaaagac      2760
ataatccggg ctataaggag gtaagcttga tctagagcgg ccgcggggat ccagacatga      2820
taagatacat tgatgagttt ggacaaacca caactagaat gcagtgaaaa aaatgcttta      2880
tttgtgaaat ttgtgatgct attgctttat ttgtaaccat tataagctgc aataaacaag      2940
ttaacaacaa caattgcatt catttttatgt ttcaggttca ggggggaggtg tgggaggttt    3000 tttcggatcc tctagagtcg acaattattt catttaataa catatagccc aaagacctct      3060
atgaacattt agtttcccgt atactcaacg gcgcgtgtac acacaagggc gaattccaca      3120
gtggatatca agcttaatta agtaccgagc tcgaattggc gcgccaggtc aattccctgg      3180
cattatgccc agtacatgac cttatgggac tttcctactt ggcagtacat ctacgtatta     3240
```

-continued

```
gtcatcgcta ttaccatggt gatgcggttt tggcagtaca tcaatgggcg tggatagcgg    3300
tttgactcac ggggatttcc aagtctccac cccattgacg tcaatgggag tttgttttgg    3360
caccaaaatc aacgggactt tccaaaatgt cgtaacaact ccgccccatt gacgcaaatg    3420
ggcggtaggc gtgtacggtg ggaggtctat ataagcagag ctcgtttagt gaaccgtcag    3480
atcgcctgga gacgccatcc acgctgtttt gacctccata gaagacaccg ggcgcgccgg    3540
atccatgggc cccagacctt ctaccaagaa cccagtacct atgatgctga ctgtccgagt    3600
cgcgctggta ctgagttgca tctgtccggc aaactccatt gatggcaggc ctcttgcggc    3660
tgcaggaatt gtggttacag agacaaagc cgtcaacata tacacctcat cccagacagg    3720
atcaatcata gttaagctcc tcccgaatct gcccaaggat aaggaggcat gtgcgaaagc    3780 cccccttggat gcatacaaca ggacattgac cactttgctc accccccttg gtgactctat    3840
ccgtaggata caagagtctg tgactacatc tggaggggggg agacagggggc gccttatagg    3900 cgccattatt ggcggtgtgg ctcttggggt tgcaactgcc gcacaaataa cagcggccgc    3960
agctctgata caagccaaac aaaatgctgc caacatcctc cgacttaaag agagcattgc    4020
cgcaaccaat gaggctgtgc atgaggtcac tgacggatta tcgcaactag cagtggcagt    4080
tgggaagatg cagcagtttg ttaatgacca atttaataaa acagctcagg aattagactg    4140
catcaaaatt gcacagcaag ttggtgtaga gctcaacctg tacctaaccg aattgactac    4200
agtattcgga ccacaaatca cttcacctgc tttaaacaag ctgactattc aggcacttta    4260
caatctagct ggtggaaata tggattactt attgactaag ttaggtgtag ggaacaatca    4320
actcagctca ttaatcggta gcggcttaat caccggtaac cctattctat acgactcaca    4380
gactcaactc ttgggtatac aggtaactct accttcagtc gggaacctaa ataatatgcg    4440
tgccacctac ttggaaacct tatccgtaag cacaaccagg ggatttgcct cggcacttgt    4500
cccaaaagtg gtgacacagg tcggttctgt gatagaagaa cttgacacct catactgtat    4560
agaaactgac ttagatttat attgtacaag aatagtaacg ttccctatgt cccctggtat    4620
ttattcctgc ttgagcggca atacgtcggc ctgtatgtac tcaaagaccg aaggcgcact    4680
tactacacca tacatgacta tcaaaggttc agtcatcgcc aactgcaaga tgacaacatg    4740
tagatgtgta aacccccccgg gtatcatatc gcaaaactat ggagaagccg tgtctctaat    4800
agataaacaa tcatgcaatg tttttatcctt aggcgggata actttaaggc tcagtgggga    4860
attcgatgta acttatcaga agaatatctc aatacaagat tctcaagtaa taataacagg    4920
caatcttgat atctcaactg agcttgggaa tgtcaacaac tcgatcagta atgctttgaa    4980
taagttagag gaaagcaaca gaaaactaga caaagtcaat gtcaaactga ctagcacatc    5040
tgctctcatt acctatatcg ttttgactat catatctctt gttttttggta tacttagccc    5100 gattctagca tgctacctaa tgtacaagca aaaggcgcaa caaaagacct tattatggct    5160
tgggaataat actctagatc agatgagagc cactacaaaa atgtgaggat ctctcgagga    5220
attctagatc ccacgtcact attgtatact ctatattata ctctatgtta tactctgtaa    5280
tcctactcaa taaacgtgtc acgcctgtga aaccgtacta agtctcccgt gtcttcttat    5340
caccatcagg tgcatcctc gcccaggctg tcaatcatgc cggtatcgat ccagtagca    5400 ccggccccac gctgacaacc cactcttgca gcgttagcag cgcccctctt aacaagccga    5460
cccccaccag cgtcgcggtt actaacactc ctctcccc                           5498
```

<210> SEQ ID NO 2
<211> LENGTH: 2459

```
<212> TYPE: DNA
<213> ORGANISM: Artificial Sequence
<220> FEATURE:
<223> OTHER INFORMATION: Expression cassette 3
<220> FEATURE:
<221> NAME/KEY: promoter
<222> LOCATION: (20)..(701)
<223> OTHER INFORMATION: PRV gB gene promoter, extended
<220> FEATURE:
<221> NAME/KEY: gene
<222> LOCATION: (713)..(2395)
<223> OTHER INFORMATION: AIV HA H9 gene, synthetic, codon optimised
<220> FEATURE:
<221> NAME/KEY: terminator
<222> LOCATION: (2404)..(2458)
<223> OTHER INFORMATION: FHV1 Us9 gene terminator

<400> SEQUENCE: 2
agcttaatta aggcgcgcca gatctcgctg ctgcacacgt acgtggcggt ggccgccggg      60
ttccgcgcac ggcgcgcgtt ctgcgaggcc gccgcgcgcg cgggcaccgt cgtggacgag     120
cgcgagacgg gctgcttcga cgcgcacagc ttcatgaagg ccacggtgca gcgccacccc     180
gtggacgccg cgctcctccc ggcgctcacg cacaagttct tcgagctcgt caacgggccg     240
ctcttcgcgc acgacacgca cgccttcgcc cagtccccca acacggcgct ctactttgcg     300
gtggagaacg tgggcctcct gccgcacctg aaggaggagc tggcgcgctt catggtggcc     360
cgcgattggt gcgtcagtga gttccgcggc ttctaccgct tccagacggc cggcgtaacc     420
gccacccagc ggcaggcctg gcgatatatc cgcgagctgg tgctggcggt tgcagtcttc     480
aggtccgtct tccactgcgg ggacgtcgag gtcctccgcg cggatcgctt cgccggacgc     540
gacgggctgt acctgaccta cgaggcgtct tgccccgctg gtggcggtct ttggcgcggg     600
ccccgcgggc atcggcccgg gcaccacggc ggtgctggcc tcggacgtct ttggcctgct     660
ccacaccacg ctgctgctgc gcggggcgcc gtcgcgctag agatctaaag ccatggagac     720
catctccctg atgactatcc tgctcgtcgt gaccacctcc aacgccgaca agatttgcat     780
cggtcaccag tccaccaact ctaccgagac cgtggacacc ctgaccgaga ctaacgtccc     840
tgtcacccac gccaaggagc tgctgcacac tgagcacaac ggaatgctct gcgctaccaa     900
cctcggtcac ccactcatcc tggacacctg cactatcgag ggtctcatct acggcaaccc     960
ctcttgcgac ctgctcctgg gaggtcgtga gtggtcctac atcgtcgagc gtccttccgc    1020
tgtgaacggc acttgctacc ccggtaacgt ggagaacctc gaggagctcc gtactctctt    1080
ctcctcttcc tccagctacc agcgtatcca aatcttcccc gacacgatct ggaacgtgac    1140
ctacaccggt acctccaagt cctgcagcga ctctttctac cgcaacatgc gctggctgac    1200
ccagaagaac ggactgtacc ctgtgcagga cgctcagtac accaacaacc gcggaaagga    1260
catcctgttc gtctggggta tccaccaccc tcccactgac accgctcaga ccaacctgta    1320
cactcgcacc gacactacca ctagcgtcac taccgagaac ctggaccgca ctttcaagcc    1380
actgatcggt cctcgtcctc tggtgaacgg tctgatcggc aggatcaact actactggag    1440
cgtgctcaag cccggacaga ctctgagggt gcgtagcaac ggcaacctga tcgcccttg    1500 gttcggtcac gtgctgtctg agagtctca cggacgtatc ctgaagaccg acctgaactc    1560
cggtaactgc gtggtccagt gccagactga gaagggtggc ctcaactcca ctctgccctt    1620
ccacaacatc tccaagtacg ccttcggcac ctgccccaag tacatcggtg tgaagtccct    1680
gaagctcgct atcggactgc gtaacgtccc tgctaggtcc agcaggggtc tgttcggcgc    1740
tatcgctggt ttcatcgagg gtggatggcc tggtctggtg ctggttggt acggcttcca    1800
```

-continued

```
gcactctaac gaccagggtg tcggaatggc cgctgaccgt gactctactc agaaggccgt    1860
cgacaagatc acctccaagg tgaacaacat cgtcgacaag atgaacaagc agtacgagat    1920
catcgaccac gagttctccg aggtggagac tcgcctcaac atgatcaaca acaagatcga    1980
cgaccagatc caggacgtct gggcttacaa cgctgagctc ctggtgctcc tcgagaacca    2040
gaagactctg gacgagcacg acgccaacgt caacaacctc tacaacaagg tgaagcgtgc    2100
cctgggctcc aacgctatgg aggacggcaa gggttgcttc gagctctacc acaagtgcga    2160
cgaccagtgc atggagacca tcaggaacgg gacctacaac cgccgtaagt acaaggagga    2220
gagcaggctg gagcgtcaga agatcgaggg cgtcaagctg gagtctgagg gcacctacaa    2280
gatcctgact atctactcca ccgtcgcctc tagcctcgtg ctcgctatgg gcttcgctgc    2340
cttcctgttc tgggccatgt ccaacggttc ctgccgttgc aacatctgca tctaattaat    2400
taacaataaa catagcatac gttatgacat ggtctaccgc gtcttatatg gggacgaca      2459
```

```
<210> SEQ ID NO 3
<211> LENGTH: 20
<212> TYPE: DNA
<213> ORGANISM: Herpesvirus of turkeys
<220> FEATURE:
<221> NAME/KEY: primer
<222> LOCATION: (1)..(19)
<223> OTHER INFORMATION: guide RNA for UL40-41 insertion

<400> SEQUENCE: 3
acctaaagta cacgtgaatc                                                    20

<210> SEQ ID NO 4
<211> LENGTH: 20
<212> TYPE: DNA
<213> ORGANISM: Herpesvirus of turkeys
<220> FEATURE:
<221> NAME/KEY: primer
<222> LOCATION: (1)..(20)
<223> OTHER INFORMATION: guide RNA for UL44-45 insertion

<400> SEQUENCE: 4
acatcgggac gtacatcatg                                                    20

<210> SEQ ID NO 5
<211> LENGTH: 20
<212> TYPE: DNA
<213> ORGANISM: Herpesvirus of turkeys
<220> FEATURE:
<221> NAME/KEY: primer
<222> LOCATION: (1)..(20)
<223> OTHER INFORMATION: guideRNA for UL47-48 insertion

<400> SEQUENCE: 5
tggcggttac aatttccacg                                                    20

<210> SEQ ID NO 6
<211> LENGTH: 20
<212> TYPE: DNA
<213> ORGANISM: Herpesvirus of turkeys
<220> FEATURE:
<221> NAME/KEY: primer
<222> LOCATION: (1)..(20)
<223> OTHER INFORMATION: guide RNA for UL54-LORF4 insertion

<400> SEQUENCE: 6
ttagatttcc ggacagcctg                                                    20
```